(12) United States Patent
Yang et al.

(10) Patent No.: US 9,057,705 B2
(45) Date of Patent: Jun. 16, 2015

(54) SURFACE-ENHANCED RAMAN SPECTROSCOPY SUBSTRATE FOR ARSENIC SENSING IN GROUNDWATER

(75) Inventors: Peidong Yang, El Cerrito, CA (US); Martin Mulvihill, Berkeley, CA (US); Andrea R. Tao, Santa Barbara, CA (US); Prasert Sinsermsuksakul, Berkeley, CA (US); John Arnold, Berkeley, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 1276 days.

(21) Appl. No.: 12/372,672

(22) Filed: Feb. 17, 2009

(65) Prior Publication Data

US 2009/0225310 A1  Sep. 10, 2009

Related U.S. Application Data

(60) Continuation-in-part of application No. 12/326,616, filed on Dec. 2, 2008, now abandoned, which is a division of application No. 11/336,662, filed on Jan. 20, 2006, now abandoned, which is a continuation of application No. PCT/US2004/024290, filed on Jul. 28, 2004.

(60) Provisional application No. 60/490,975, filed on Jul. 28, 2003, provisional application No. 61/028,874, filed on Feb. 14, 2008.

(51) Int. Cl.
| | |
|---|---|
| *H01L 51/05* | (2006.01) |
| *G01N 21/65* | (2006.01) |
| *H01L 29/51* | (2006.01) |
| *H01L 29/06* | (2006.01) |
| *H01L 29/775* | (2006.01) |
| *H01L 21/02* | (2006.01) |

(52) U.S. Cl.
CPC .......... *G01N 21/658* (2013.01); *H01L 29/0676* (2013.01); *H01L 29/518* (2013.01); *H01L 29/775* (2013.01); *H01L 21/0245* (2013.01)

(58) Field of Classification Search
CPC .............. H01L 29/518; H01L 21/3185; H01L 21/28185; H01L 21/02381; H01L 21/0245; H01L 21/02532; H01L 21/02554; H01L 21/658
USPC ..................... 257/1, 9, 327, 40, 146, E21.306, 257/E21.582; 438/775, 597; 356/301; 977/700
See application file for complete search history.

(56) References Cited

U.S. PATENT DOCUMENTS

| | | | | |
|---|---|---|---|---|
| 6,017,390 | A  * | 1/2000 | Charych et al. | 117/68 |
| 6,262,129 | B1 * | 7/2001 | Murray et al. | 516/33 |
| 6,284,310 | B2 | 9/2001 | Picard | |

(Continued)

OTHER PUBLICATIONS

F. Kim et al. Langmuir-Blodgett nanorod assembly. J. Am. Chem. Soc., vol. 123, pp. 4360-4361 (2001).

*Primary Examiner* — Thinh T Nguyen
(74) *Attorney, Agent, or Firm* — John P. O'Banion

(57) ABSTRACT

A surface-enhanced Raman spectroscopy (SERS) substrate formed from a plurality of monolayers of polyhedral silver nanocrystals, wherein at least one of the monolayers has polyvinypyrrolidone (PVP) on its surface, and thereby configured for sensing arsenic is described. Highly active SERS substrates are formed by assembling high density monolayers of differently shaped silver nanocrystals onto a solid support. SERS detection is performed directly on this substrate by placing a droplet of the analyte solution onto the nanocrystal monolayer. Adsorbed polymer, polyvinypyrrolidone (PVP), on the surface of the nanoparticles facilitates the binding of both arsenate and arsenite near the silver surface, allowing for highly accurate and sensitive detection capabilities.

11 Claims, 33 Drawing Sheets

(56) References Cited

U.S. PATENT DOCUMENTS

| | | |
|---|---|---|
| 6,440,637 B1 | 8/2002 | Choi et al. |
| 6,660,058 B1 * | 12/2003 | Oh et al. ............... 75/351 |
| 7,585,349 B2 * | 9/2009 | Xia et al. ............... 75/371 |
| 7,892,734 B2 * | 2/2011 | Lu et al. ............... 435/6.11 |
| 2002/0145792 A1 * | 10/2002 | Jacobson et al. ............ 359/296 |
| 2003/0124259 A1 * | 7/2003 | Kodas et al. ............ 427/376.6 |
| 2003/0228682 A1 * | 12/2003 | Lakowicz et al. ......... 435/287.2 |
| 2005/0056118 A1 * | 3/2005 | Xia et al. ............... 75/330 |

\* cited by examiner

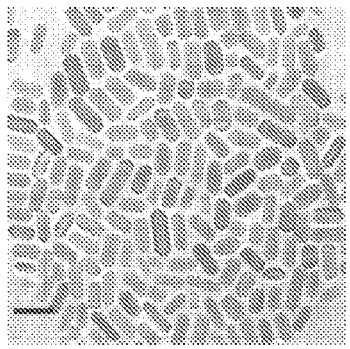 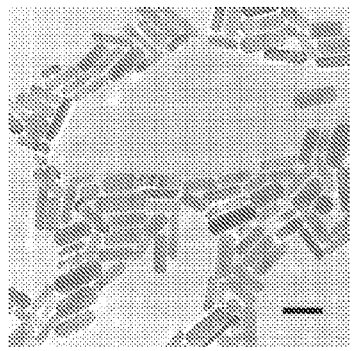 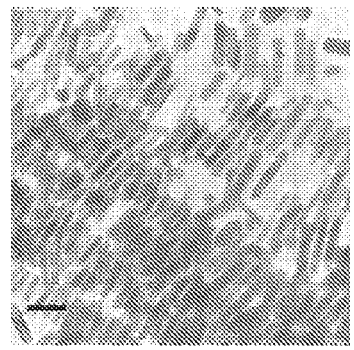
FIG. 12A   FIG. 12B   FIG. 12C
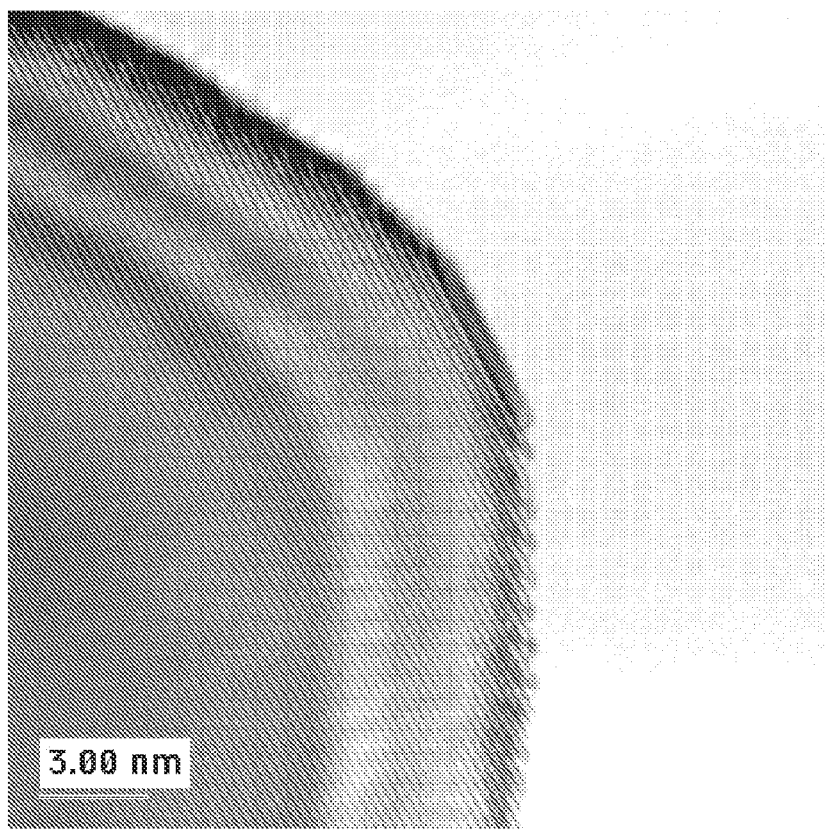
FIG. 13

SURFACE-ENHANCED RAMAN SPECTROSCOPY SUBSTRATE FOR ARSENIC SENSING IN GROUNDWATER

CROSS-REFERENCE TO RELATED APPLICATIONS

This application claims priority from U.S. provisional application Ser. No. 61/028,874 filed on Feb. 14, 2008, incorporated herein by reference in its entirety, and is a continuation in part of U.S. application Ser. No. 12/326,616 filed on Dec. 2, 2008, incorporated herein by reference in its entirety, which is a divisional of U.S. application Ser. No. 11/336,662 filed on Jan. 20, 2006, incorporated herein by reference in its entirety, which claims priority from, and is a 35 U.S.C. §111 (a) continuation of, PCT international application serial number PCT/US04/24290 filed on Jul. 28, 2004, which designates the U.S., incorporated herein by reference in its entirety, which claims priority from U.S. provisional application Ser. No. 60/490,975 filed on Jul. 28, 2003, incorporated herein by reference in its entirety.

This application is also related to PCT International Publication Number WO 2005/059952 B2, incorporated herein by reference in its entirety.

STATEMENT REGARDING FEDERALLY SPONSORED RESEARCH OR DEVELOPMENT

This invention was made with Government support under Grant Number DE-FG02-02ER46021 awarded by the Department of Energy (DOE) and Grant Number ESO4705 awarded by the National Institutes of Health (NIH). The Government has certain rights in the invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to surface-enhanced Raman spectroscopy (SERS) sensors, and more particularly to a SERS sensor for arsenic sensing and its method of fabrication.

2. Description of Related Art

Techniques for directing the assembly of metal or semiconductor quantum dots into superstructures have been pursued over the years. Few studies have addressed the organization of one-dimensional nanoscale building blocks such as nanotubes, nanowires, and nanorods into ordered structures except for the 3-dimensional spontaneous superlattice formation of nanorods made from certain materials. On the other hand, Kim, F. et al., "Langmuir-Blodgett Nanorod Assembly", J. Am. Chem. Soc. 123, 4386-4389 (2001), incorporated herein by reference, describes a method for fabricating a 2-dimensional monolayer assembly of $BaCrO_4$ nanorods using the Langmuir-Blodgett technique.

Various researchers have successfully prepared Langmuir-Blodgett films of spherical nanoparticles such as Ag, Au, and CdS. Typically, the surface of the nanocrystals are functionalized by organic molecules (usually long alkyl chains) in order to prevent particle aggregation and also to ensure the floating of the nanoparticles on the subphase surface (usually water). The nanoparticles are then dispersed in organic solvents such as toluene, and this solution is spread drop-wise onto the subphase surface. The nanoparticles form a monolayer on the water-air interface, which is slowly compressed. This monolayer can be transferred during the compression using either horizontal or vertical liftoff to substrates such as TEM grid or Si wafer to be inspected under electron and optical microscopes. For spherical nanoparticles, the particles form a gas phase at low densities, where the monolayer is highly compressible without significant increase in the surface pressure. Depending on the particle size, the length of the capping ligand, and the surface pressure, various microscopic structures of islands, wires, and rings composed of the nanoparticles can be formed. As the monolayer is compressed, the nanoparticles start to form a condensed phase, usually a hexagonally close packed structure due to the isotropic inter-particle interactions.

Nanoscale science, however, is about assembling matter at multiple length scales, from atomic and molecular species to individual nanoscale building blocks such as nanocrystals, nanorods and nanowires, then from these individual nanoscale building blocks to higher-level functional assemblies and systems. This hierarchical process covers length scale of several orders, from Å to micrometer or larger. The past decades have witnessed great progress in the direction of synthesizing nanocrystals of various compositions and sizes. Significant progress has been made in the area of nanowire synthesis and device application. Successful alignment and patterning of nanowires would significantly impact many areas such as nanoscale electronics, optoelectronics and molecular sensing. A grand challenge, however, resides in the hierarchical integration of the nanoscale building blocks into functional assemblies and ultimately to a system.

Unlike the traditional lithographical process where precise placement of certain elements or devices is embedded in the designing process, the precise placement of nanoscale building blocks on the right place with right configuration and with exceedingly high densities represents a daunting task for researchers in this field.

Nanoparticles have attracted a great deal of attention due to their potential applications in optics, electronics, and catalysis. Different methods have been developed to synthesize metallic and semiconductor nanoparticles of different sizes. In the synthesis of new materials based on an ordered assembly of nanoparticles, three significant factors are important in determining the interactions between the nanoparticles and ultimately their superstructures, namely the shape and size distributions of the nanoparticles, and the surface functionality of the nanoparticles. A major motivation for research in this field remains the challenge to understand how ordered or complex structures form by self- or directed-assembly, and how such processes can be monitored/controlled in order to prepare structures with a pre-determined geometry/superstructure.

A prerequisite for nanostructure preparation via the assembly route is the availability of sufficiently stable building blocks that are highly uniform in size and shape. Techniques for directing the assembly of metal or semiconductor quantum dots into novel superstructures have been extensively pursued over the past decades. Impressive accomplishments in the area of self-assembly of metallic silver and gold nanoparticles, semiconductor CdSe and $Ag_2S$ quantum dots and spherical nanoparticles have been reported. This is due to the possibility of obtaining these spherical nanoparticles as highly monodispersed and stable products. In spite of the large volume of research on the self-assembly of quantum dots, however, little attention has been devoted to the self-assembly of rod-shaped nanoparticles (nanorods) and particles with other different shapes (prisms, hexagons, cubes). This is partly due to the fact that there is no chemistry available for preparing these highly uniform facetted nanocrystals.

After decades of research, the size control of the metal and semiconductor nanocrystals is now well-established. The deterministic shape control is, however, still in its infancy although recent efforts into nanorod synthesis have resulted in some very exciting progress. In addition, there has been progress toward shape control of II-IV compound nanocrystals, where easy axis (6-fold symmetry) exists within the crystal structure and has profound impact on the resulting nanocrystal growth habits. In general, however, the mechanism of shaped nanocrystal growth, particularly for those metal systems, is still much elusive and currently under hot debate.

Nanocrystal shape control is still a highly empirical process due to the lack of fundamental understanding of the complex growth process with multiple synthetic parameters. One known approach to shape control is to use surfactants during the metal reduction and particle growth. The surfactant has a role to control the crystal shapes by attaching to selected crystal surface during the growth. Of course, the surfactants also stabilize the metal particles and avoid the undesirable aggregation. In this regard, some linear polymers are recently found to be highly effective to control the crystal shapes. For example, polyacrylate, poly-(N-vinyl-2-pyrrolidone) and polyvinyl alcohol have been used to control the metal particle shapes with a reasonable yield. A main advantage of this surfactant/polymer approach for shaped crystal synthesis is the relative large yield and its potential to produce high purity products.

Besides the surfactant approach, one additional important factor that could determine the final crystal shapes is the addition of foreign ions. For example, it has been found that different ions and ionic strength could be used to modulate the copper nanocrystal shapes. It has also been found that a small amount of silver addition is critical for the formation of gold nanorods in an electrochemical process.

Surface-enhanced Raman spectroscopy (SERS) has previously been employed for chemically specific and sensitive detection of molecular monolayers, small biological molecules, trace-level explosives, organic groundwater contaminants, and single molecules. Typical detection signal enhancements are around $10^9$ greater than sensing performed without a metallic substrate.

Therefore, there is a need for a method of assembling monolayers of nanostructures other than spherical nanoparticles. There is also a need for a method of controlling shape synthesis of metal nanostructures and mediating the interaction among these particles to form different 2-dimensional (2D) or 3-dimensional (3D) superstructures. The resultant superstructures are of importance for their tunable collective physical properties (e.g. optical, magnetic and catalytic properties), where inter-object separation, shape and interfacial structure enable the tuning of properties. A further need is increased Raman enhancement for SERS detection with use of nanostructured silver surfaces.

BRIEF SUMMARY OF THE INVENTION

The present invention addresses the foregoing needs by adapting the Langmuir-Blodgett (LB) technique for assembly of monolayers of nanostructures other than spherical nanoparticles. Surface functionalization of these nanostructures is used to mediate the interaction among these particles to form different 2-dimensional (2D) or 3-dimensional (3D) superstructures.

In one beneficial embodiment of the invention, a method for fabricating a monolayer of nanostructures comprises the steps of forming a plurality of nanostructures, rendering the nanostructures hydrophobic, dispersing the hydrophobic nanostructures onto a water surface of a Langmuir-Blodgett trough and forming a monolayer film of ordered nanostructures, and compressing the monolayer film. In a further embodiment, the shape of the nanostructures is controlled and selected from the group consisting essentially of cube-shaped, plate-shaped, rod-shaped, triangle-shaped, and hexagon-shaped.

In another beneficial embodiment of the invention, a method for fabricating monolayer of silver nanowires comprises forming silver nanowires using a solution-phase polyol process wherein said nanowires have faceted cross-sections, rendering the nanowires hydrophobic, dispersing the hydrophobic nanowires onto a water surface of a Langmuir-Blodgett trough and forming a monolayer film of nanowires that exhibit substantial parallel alignment, and compressing the monolayer nanowire film and forming a monolayer through an insulator-to-metal transition.

In the case of the formation of silver nanowires, the diameters of approximately 50 nm are achievable. The nanowires can have various cross-sectional shapes, including pentagonal cross-sections, and the tips can be pyramidal with vertices as sharp as 2 nm. The nanowires can be formed as close-packed as parallel arrays with their longitudinal axes aligned perpendicular to the compression direction.

In the foregoing embodiments, the area of the compressed monolayer film can vary to as much as 20 $cm^2$ or greater, and the monolayer film beneficially can be deposited onto a substrate for support and structure formation. The substrate can be selected from various materials such as silicon wafers, glass slides, and polymer and other substrates.

The monolayer is capable of functioning as a surface enhanced Raman Spectroscopy (SERS) substrate for molecular sensing, and is suitable for molecular-specific sensing utilizing vibrational signatures. Optionally, the monolayer can be configured for the detection of 2,4-dinitrotoluene (2,4-DENT), for use as an interconnect, as a component in a multilayer structure.

Optionally, the monolayer can be embedded in polydimethylsiloxane (PDMS), in which case the embedded monolayer is capable of functioning as a simple wire-grid optical polarizer.

An aspect of the present invention is assembly of monolayers of aligned silver nanowires using the Langmuir-Blodgett technique. In one embodiment, the monolayers have an area over 20 $cm^2$. In one embodiment the nanowires are ~50 nm in diameter. In one embodiment, the nanowires possess pentagonal cross-sections. In one embodiment, the nanowires possess pyramidal tips. In one embodiment the pyramidal tips have vertices as sharp as 2 nm.

Another aspect of the invention is assembly of monolayers of aligned silver nanowires which are close-packed and aligned parallel to each other using the Langmuir-Blodgett technique.

A further aspect of the invention is assembly of monolayers of aligned silver nanowires which are close-packed as parallel arrays with their longitudinal axes aligned perpendicular to the compression direction.

Another aspect of the invention is assembly of monolayers of aligned silver nanowires that serve as surface enhanced Raman Spectroscopy substrates.

Another aspect of the invention is assembly of monolayers of aligned silver nanowires that are suitable for molecular-specific sensing utilizing vibrational signatures.

Another aspect of the invention is to embed monolayers of silver nanowires within polydimethylsiloxane (PDMS).

Another aspect of the invention is to embed multilayers of silver nanowires within polydimethylsiloxane (PDMS).

Another aspect of the invention is to form flexible nanowire-polymer composites that can serve as simple wire-grid optical polarizers.

Another aspect of the invention is to provide monolayer structures suitable for chemical and biological sensing.

According to a further aspect of the invention, aligned silver nanowire monolayers are used as surface-enhanced Raman spectroscopy (SERS) substrates for molecular sensing. In one embodiment, an aligned silver nanowire monolayer is configured for the detection of 2,4-dinitrotoluene (2,4-DENT).

The use of the nanowire monolayer as SERS substrates has several advantages. First, the surface properties of the nanowire monolayer are highly reproducible and well-defined as compared to other systems. Second, several unique features of the nanowires, such as sharp vertices, non-circular pentagonal cross-sections, and inter-wire coupling, may lead to larger field enhancement factors, offering higher sensitivity under optimal conditions. In addition, strong wire coupling within the monolayer enables SERS experiments with a broad selection of excitation sources. Lastly, these monolayers can readily be used for molecular detection in either an air-borne or a solution environment. Hence, nanowire-based sensors the monolayer of the present invention may be particularly useful in chemical and biological warfare detection, national and global security, as well as medical detection applications.

Accordingly, another aspect of the invention comprises high density nanoscale interconnects, sensor arrays, and multilayer structures.

Another aspect of the invention is to transfer monolayers according to the present invention to any desired substrates, including silicon wafers, glass slides, and polymer substrates.

A still further aspect of the invention is to form 2-dimensional superstructures from shape controlled nanocrystals and nanowires using the Langmuir-Blodgett technique.

Another aspect of the invention is to assemble cube-shaped, plate-shaped, rod-shaped, triangle-shaped, and hexagon-shaped nanocrystals into 2-dimensional superstructures using the Langmuir-Blodgett technique.

Another aspect of the invention is to form monolayer structures that can be used in lithography applications.

Yet another aspect of the invention is sensor, comprising a surface-enhanced Raman spectroscopy (SERS) substrate formed from a plurality of monolayers of polyhedral silver nanocrystals, wherein at least one of the monolayers has polyvinypyrrolidone (PVP) on its surface. When irradiated with light, these nanoscale features are known to localize electromagnetic radiation at their surface, resulting in the creation of "hot spots" where Raman signal enhancement is greatest.

Another aspect of the invention is a method of forming a sensor, comprising forming a surface-enhanced Raman spectroscopy (SERS) substrate from a plurality of monolayers of polyhedral silver nanocrystals, and applying polyvinypyrrolidone (PVP) to the surface of at least one of the monolayers.

In one embodiment, highly active SERS substrates are produced by assembling high density monolayers of differently shaped silver nanocrystals onto a solid support. SERS detection is performed directly on this substrate by placing a droplet of the analyte solution onto the nanocrystal monolayer. Adsorbed polymer, polyvinypyrrolidone (PVP), on the surface of the nanoparticles facilitates the binding of both arsenate and arsenite near the silver surface, allowing for highly accurate and sensitive detection capabilities.

A further aspect of the invention is a sensor, comprising: a surface-enhanced Raman spectroscopy (SERS) substrate having a plurality of high density (close-packed) monolayers of differently shaped polyhedral silver nanocrystals on a solid support; at least one said monolayer comprising a nanocrystal monolayer having an exposed silver surface; an analyte solution of polyvinypyrrolidone (PVP) on the exposed silver surface of the nanocrystal monolayer; wherein said analyte solution facilitates the binding of both arsenate and arsenite near the exposed silver surface.

In one embodiment, the nanocrystals are shape-controlled using Langmuir-Blodgett (LB) compression.

In another embodiment, the nanocrystals have a shape selected from the group consisting of cubes, cuboctahedra, octahedra and other polyhedral shapes.

In yet another embodiment, incident electromagnetic radiation is localized on the silver surface.

In a further embodiment, the PVP is grafted onto the silver surface by polyhedral nanocrystal synthesis.

Another aspect of the invention is a method of forming a sensor, comprising: forming a surface-enhanced Raman spectroscopy (SERS) substrate having a plurality of high density (close-packed) monolayers of differently shaped polyhedral silver nanocrystals on a solid support; at least one monolayer comprising a nanocrystal monolayer having an exposed silver surface; and exposing the silver surface of the nanocrystal monolayer to an analyte solution of polyvinypyrrolidone (PVP); wherein the analyte solution facilitates the binding of both arsenate and arsenite near the exposed silver surface.

Another aspect of the invention is a method of forming a sensor, comprising: preparing colloidal solutions of different polyhedral shapes; carrying out Langmuir-Blodgett assembly to form nanocrystal monolayers; transferring the nanocrystal monolayers to silicon supports; exposing the nanocrystal substrates to analyte molecules by incubation and subsequent Raman detection in solution.

In one embodiment, Raman detection is performed using a Renishaw micro-Raman system using a 532 nm diode-pumped solid state laser as an excitation source, with an estimated power of −20 mW, and performing Raman signal collection in reflectance mode using a 50x objective.

Chemical sensing of arsenic ions, a low-level toxin found in ground water, with detection limits as low as 1.8 ppb ws performed with the surface-enhanced Raman spectroscopy (SERS) of the present invention. Analyte molecules near nanostructured metallic surfaces experience huge enhancements in Raman scattering cross-sections, typically orders of magnitude higher than expected.

Yet another aspect is a sensor, comprising a substrate having at least one high-density monolayer of polyhedral silver nanocrystals, wherein each of the nanocrystals comprise a layer of polyvinypyrrolidone (PVP) on its surface. The nanocrystals may have a shape selected from the group consisting of truncated cubes, cuboctahedra, truncated octahedral, and octahedra.

In one embodiment of the current aspect, the substrate comprises a plurality of close-packed monolayers of polyhedral silver nanocrystals. The nanocrystals are preferably shape-controlled using Langmuir-Blodgett compression. Additionally, the PVP is grafted onto the silver surface by polyhedral nanocrystal synthesis.

In another embodiment, prior to synthesis, the nanocrystals of the nanocrystal monolayer comprise an exposed silver surface; wherein an analyte solution of polyvinypyrrolidone (PVP) is deposited on the exposed silver surface of the nanocrystal monolayer; and wherein said analyte solution facilitates the binding of both arsenate and arsenite near the exposed silver surface.

Another aspect is an apparatus for sensing arsenic, comprising: a surface-enhanced Raman spectroscopy substrate having at least one high density monolayers of differently shaped polyhedral silver nanocrystals, wherein each of the nanocrystals comprise a layer of polyvinypyrrolidone (PVP) on its surface.

Yet another aspect is a sensor for sensing arsenic prepared by a process comprising the steps of: providing a substrate; forming at least one layer of polyhedral silver nanocrystals on the substrate; at least one said layer comprising a nanocrystal monolayer having an exposed silver surface; and exposing the silver surface of the nanocrystal layer to an analyte solution of polyvinypyrrolidone (PVP); wherein said analyte solution facilitates the binding of both arsenate and arsenite near the exposed silver surface.

In one embodiment of the current aspect, forming at least one layer comprises: preparing colloidal solutions of polyhedral shapes; carrying out Langmuir-Blodgett assembly to form nanocrystal monolayers; transferring the nanocrystal monolayers to silicon supports; exposing the nanocrystal layer to analyte molecules by incubation and subsequent Raman detection in solution.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1 is a flow diagram of an embodiment of a monolayer assembly process according to the present invention.

FIGS. 2A and B are transmission electron microscopy images of uniform Ag nanowires employed in an embodiment of the assembly process according to the present invention. The inset in FIG. 2A is an image taken from a microtomed sample, showing the pentagonal cross-sections of the nanowires. A high resolution TEM image, the upper inset in FIG. 2B, shows the sharp pentagonal pyramidal tip of a silver nanowire, as schematically illustrated in the bottom inset in FIG. 2B.

FIG. 3A through C are photographs showing the Langmuir-Blodgett (LB) nanowire assembly process of the present invention at different progressive compression stages.

FIG. 4 is a surface pressure curve recorded during the assembly process illustrated in FIG. 3.

FIG. 5A through D are scanning electron microscopy images (at different magnifications) of the silver nanowire monolayer deposited on a silicon wafer according to an embodiment of the present invention.

Figure 9:
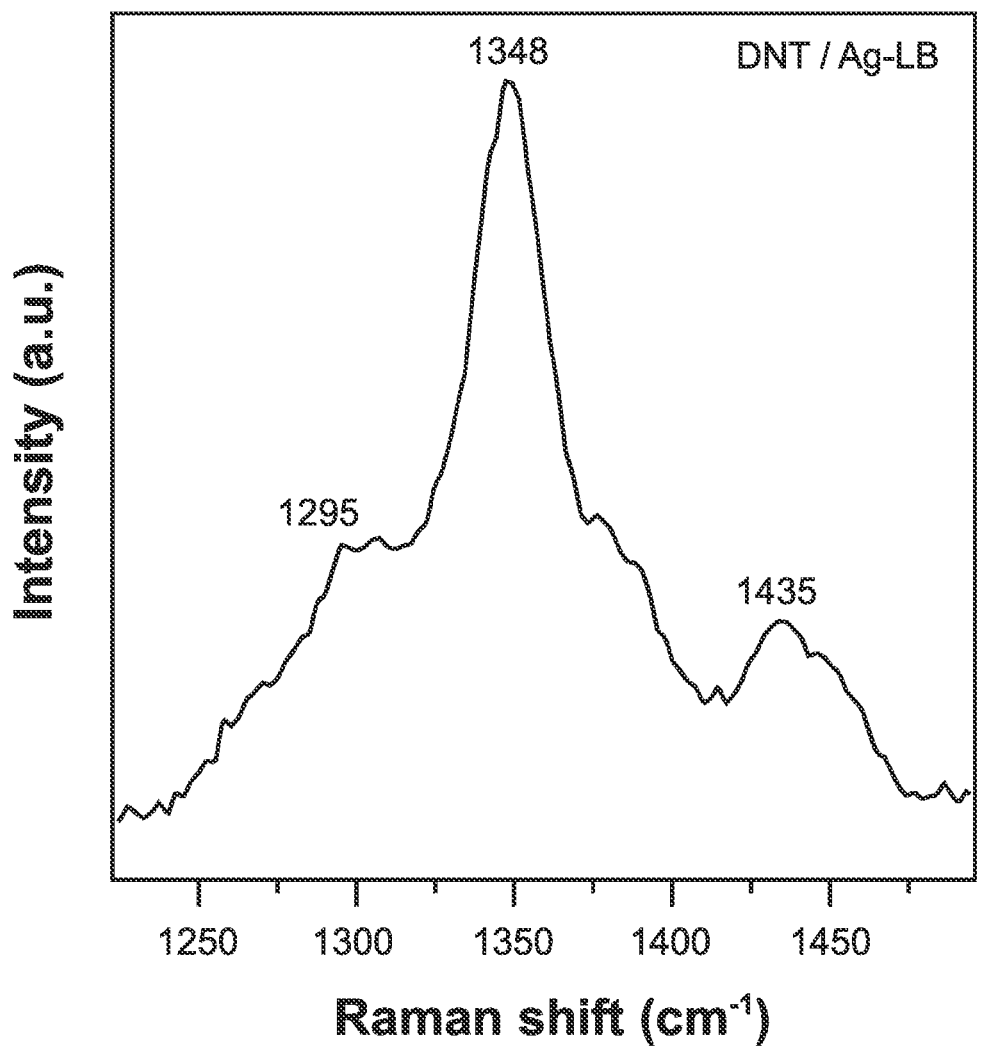

FIG. 9 is a graph illustrating surface-enhanced Raman spectroscopy on a silver nanowire monolayer assembled according to an embodiment of the invention, showing SERS spectrum of 2,4-DNT on the thiol-capped Ag nanowire monolayers after incubation for 10 min in $10^{-2}$ M 2,4-DNT/MeOH solution. The spectrum was recorded using 25 mW of 532 nm laser light. The acquisition time was 10 s.

Figure 10:
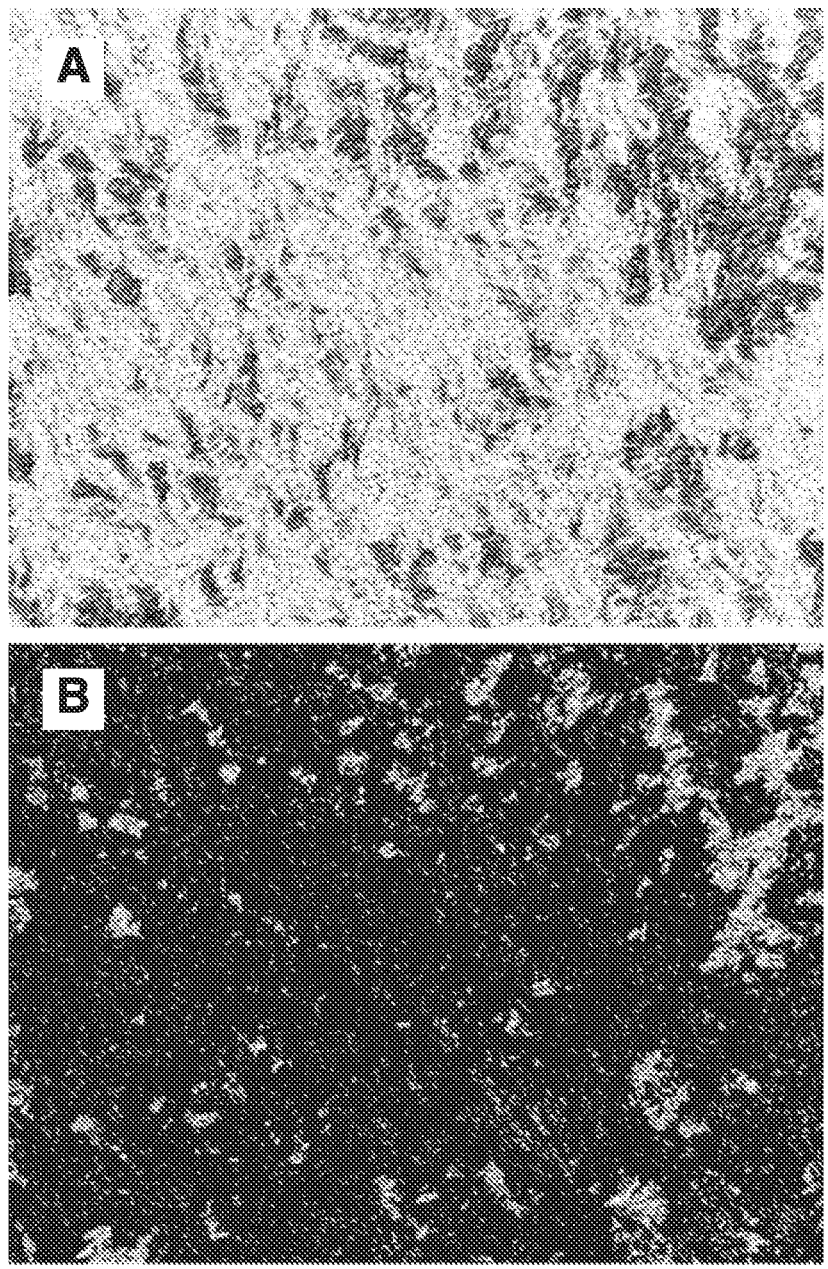

FIGS. 10A and B are optical images of a silver nanowire monolayer assembled according to an embodiment of the invention under cross-polarizer. The imaging area corresponds to 735 by 521 μm.

Figure 11:
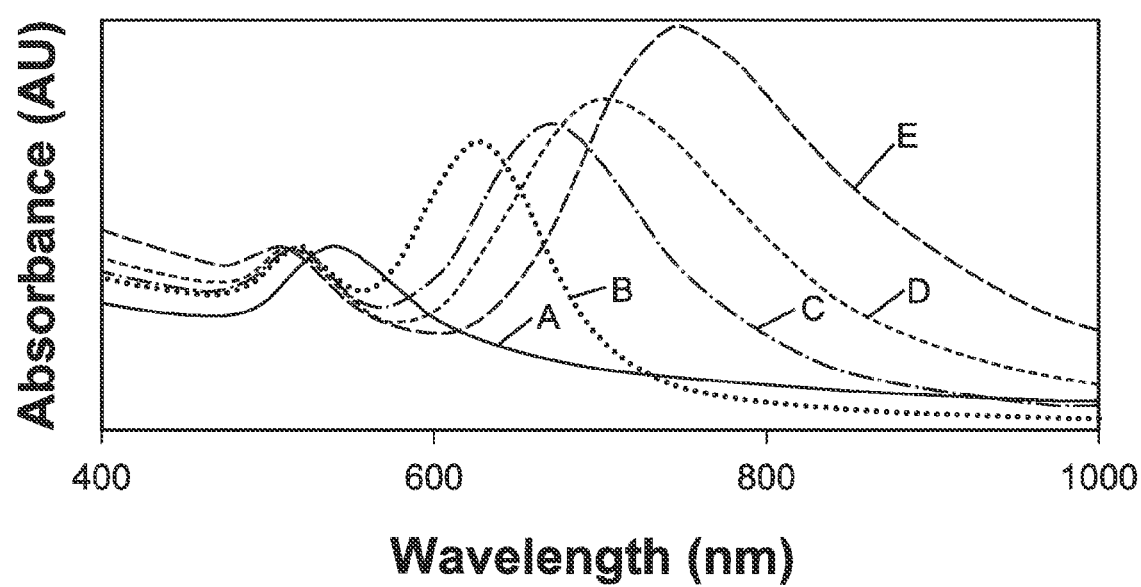

FIG. 11 illustrates the UV-VIS spectrum of five photochemically prepared gold nanorod solutions according to an embodiment of the invention where solution A was prepared with no silver ion addition, and solutions B-E were prepared with increasing amount of silver nitrate solution.

FIG. 12A-C are transmission electron microscopy (TEM) images of gold nanorods prepared with increasing amounts of silver nitrate solution addition according to an embodiment of the invention, where the bar in the lower portion of each image indicates 50 nm.

FIG. 13 is a high resolution image of a gold nanorod shown in FIG. 12.

Figure 14:
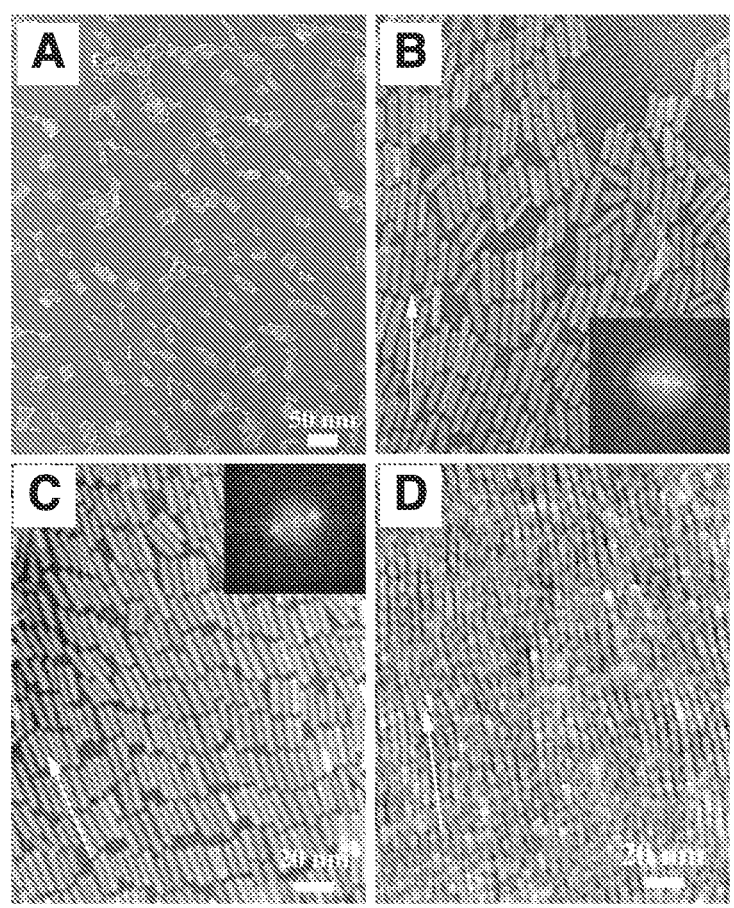

FIG. 14A-D are transmission electron microscopy images of nanorod assemblies at water/air interface at different stages of the compression according to an embodiment of the invention, where FIG. 14A shows isotropic distribution at low pressure, FIG. 14B is monolayer with nematic arrangement, FIG. 14C is a monolayer with smectic arrangement, and FIG. 14D is a nanorod multilayer with nematic configuration, and where the insets in FIG. 14B and FIG. 14D are the Fourier transform of the corresponding image.

FIG. 15A-E are schematic diagrams showing the organization of shaped nanocrystals according to an embodiment of the invention.

Figure 16:
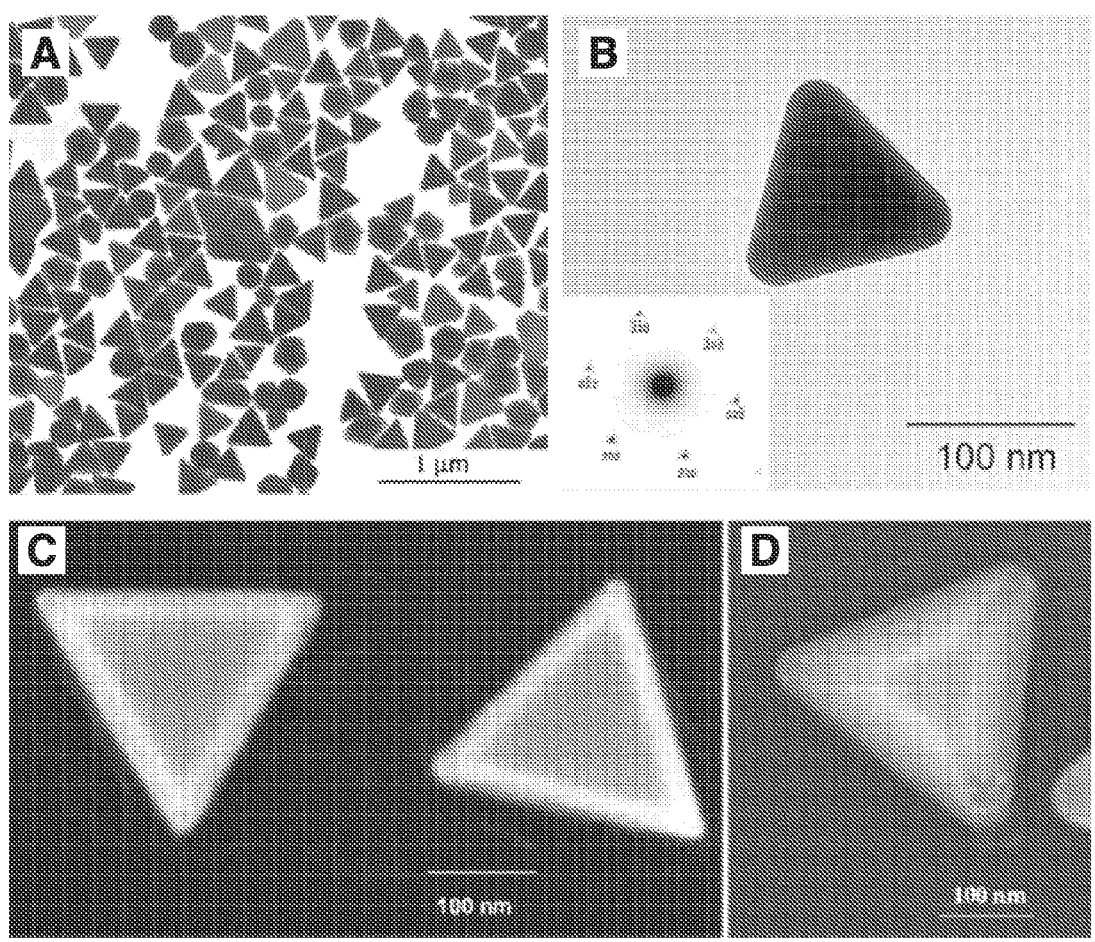

FIG. 16A-D are images of shaped nanostructures according to the present invention, wherein FIGS. 16A and B are TEM images of truncated tetrahedral gold nanoparticles and the inset in FIG. 16B is the electron diffraction pattern taken along the [111] zone axis from the particle shown in FIG. 16B, and FIGS. 16C and D are SEM images of several partially developed gold tetrahedra.

Figure 17:
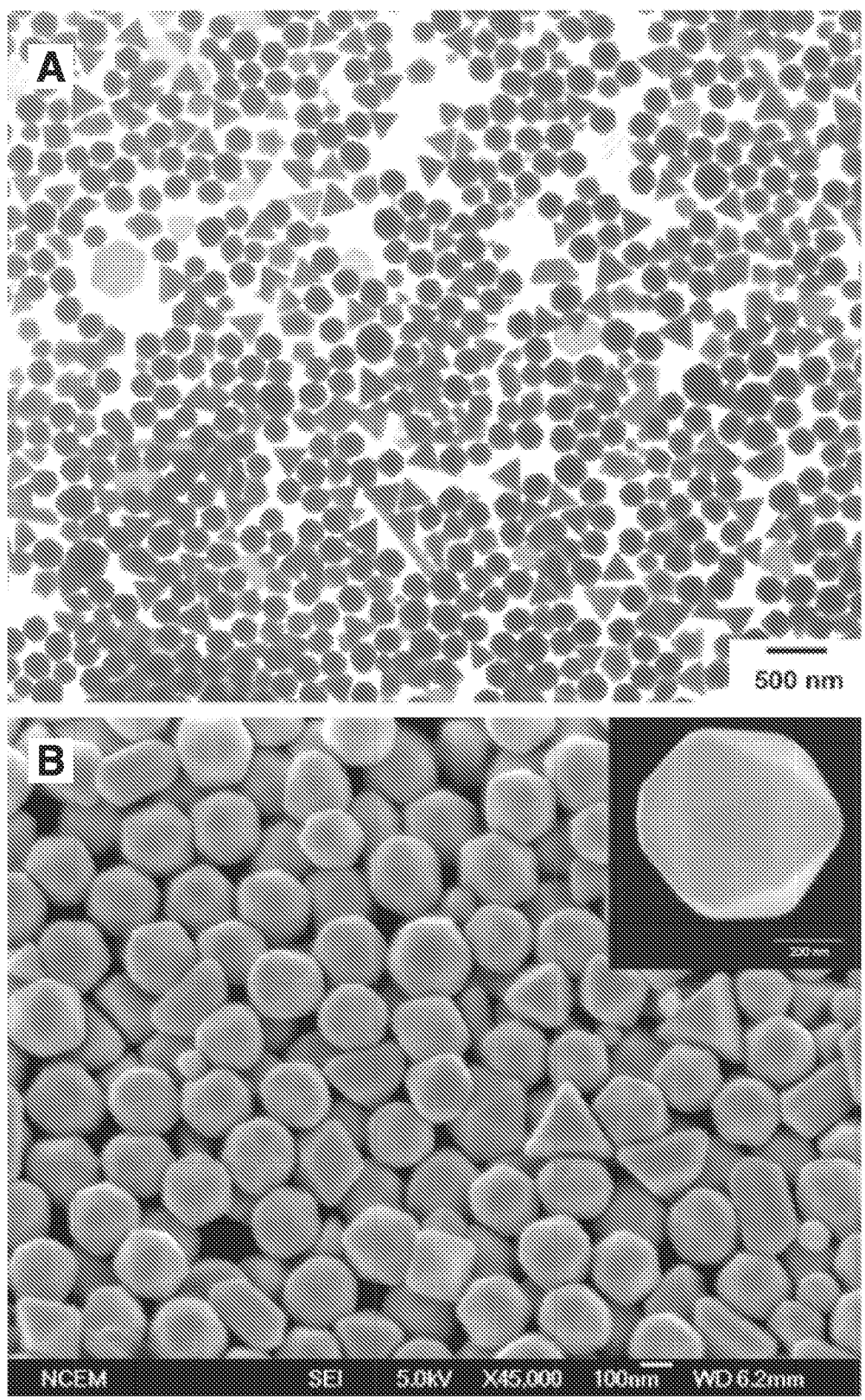

FIG. 17A-B are images of icosahedral nanocrystals according to the present invention wherein FIG. 18A is a TEM image and FIG. 17B is a SEM image of icosahedral gold nanoparticles, and wherein the inset in FIG. 17B shows clearly all {111} facets of a typical icosahedron.

FIG. 18A-C are TEM and SEM images of some minority particles observed during synthesis according to the present invention wherein FIGS. 18A and B shown decahedrons and FIG. 18C shows an octahedron.

Figure 19:
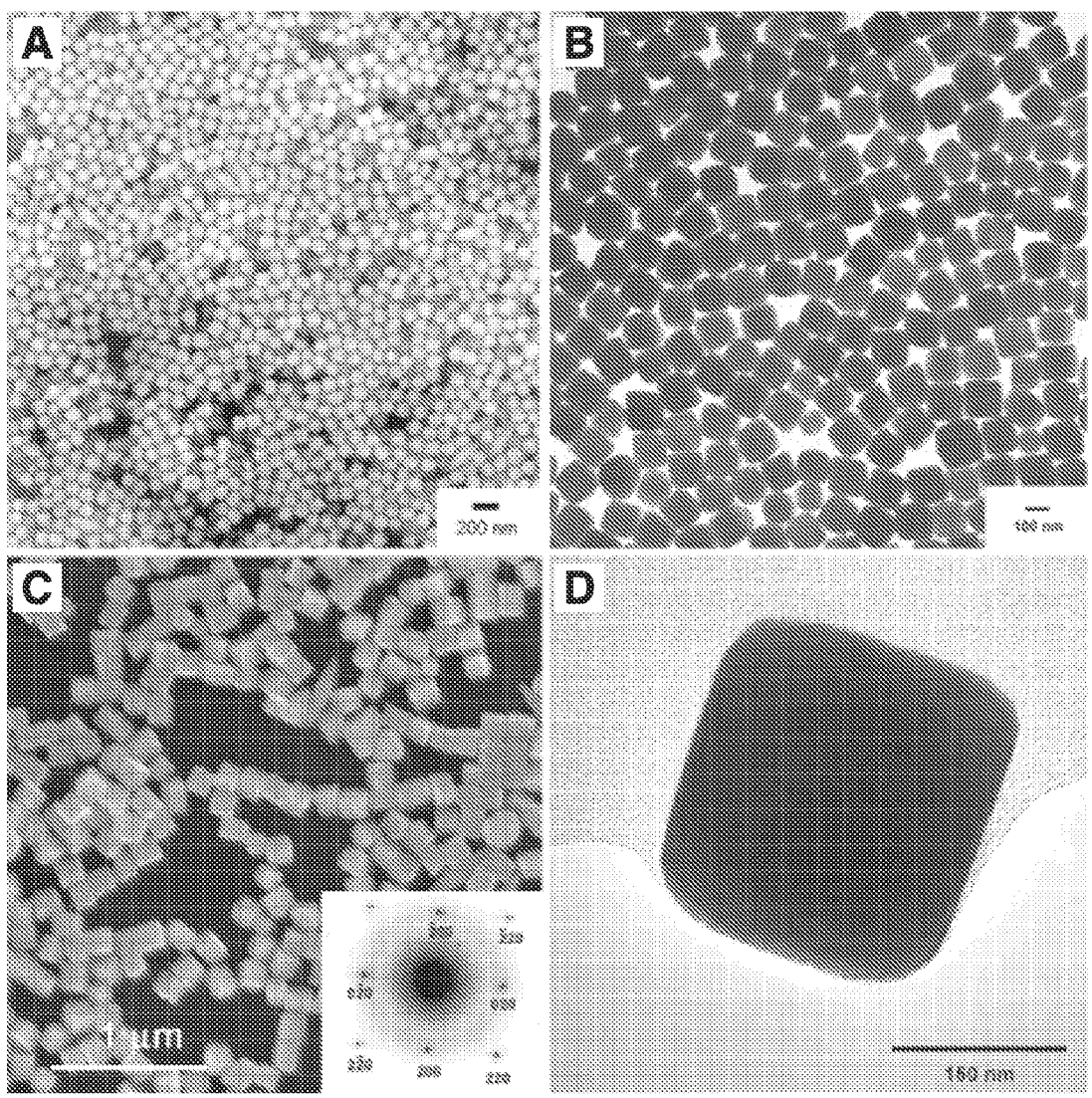

FIG. 19A-D are TEM and SEM images of gold nanocubes according to the present invention dispersed on a TEM grid and a silicon substrate wherein the inset in FIG. 19C shows the electron diffraction pattern recorded along the [100] zone axis of a gold nanocube shown in FIG. 19D.

Figure 20:
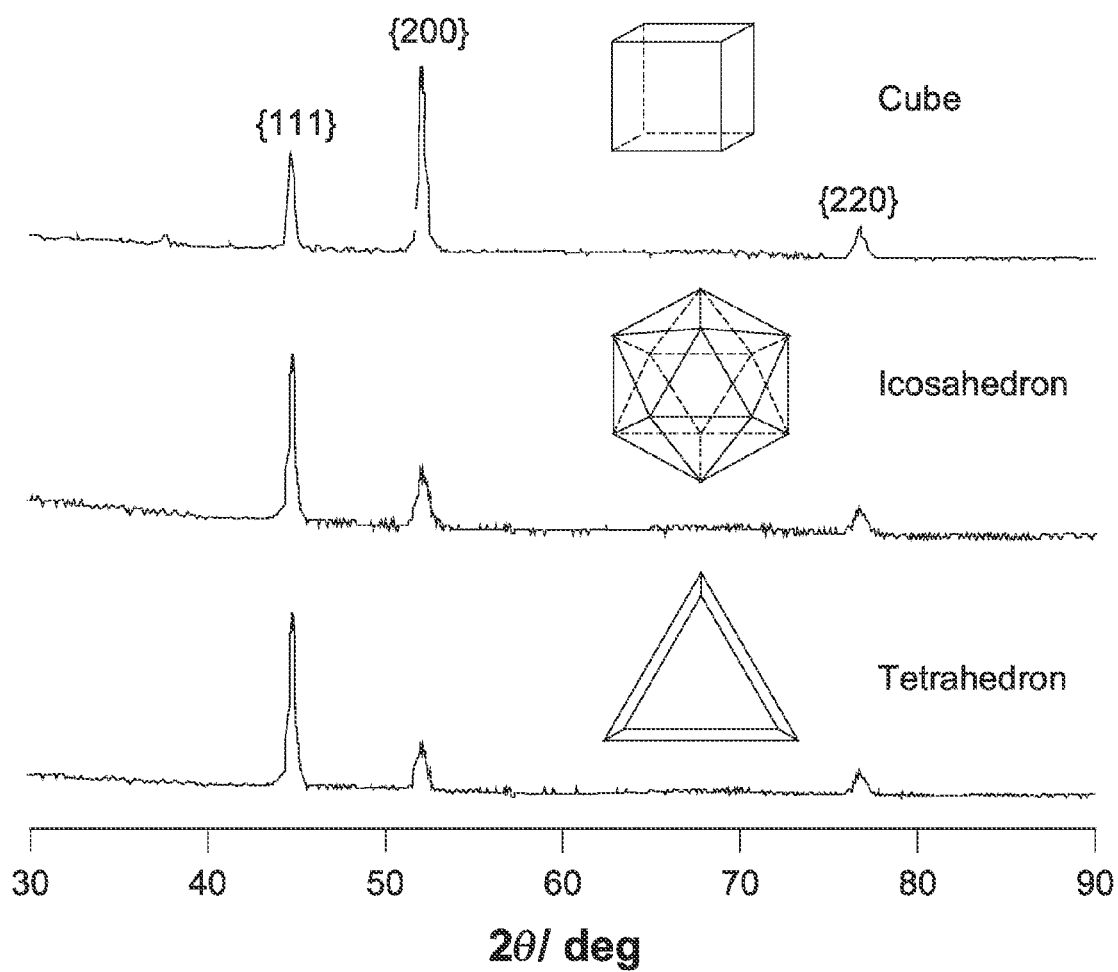

FIG. 20 shows the X-ray diffraction patterns for the three types of gold nanocrystals according to the present invention: tetrahedron, cube and icosahedron.

Figure 21:
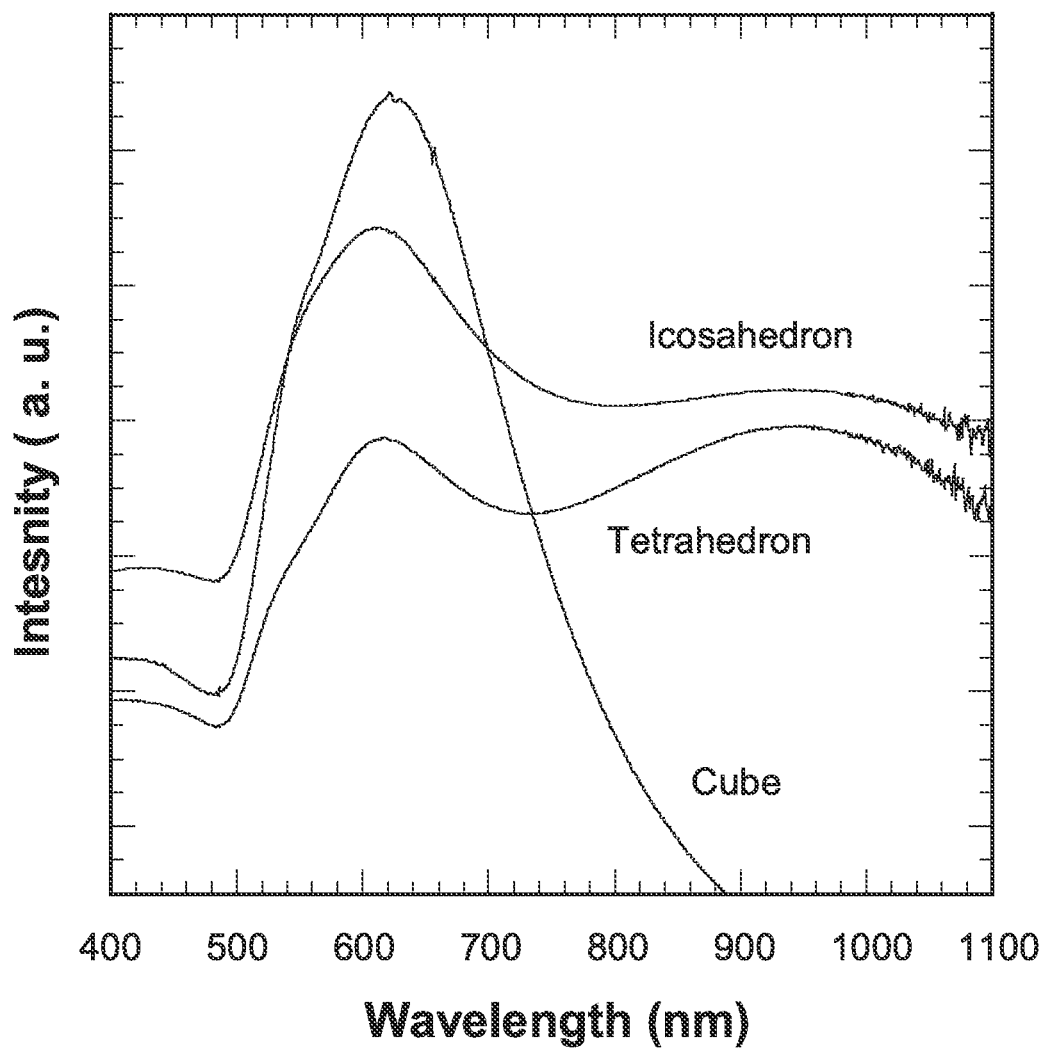

FIG. 21 shows the UV-VIS spectra for the three types of gold nanocrystals: tetrahedron, cube and icosahedron of FIG. 20.

Figure 22:
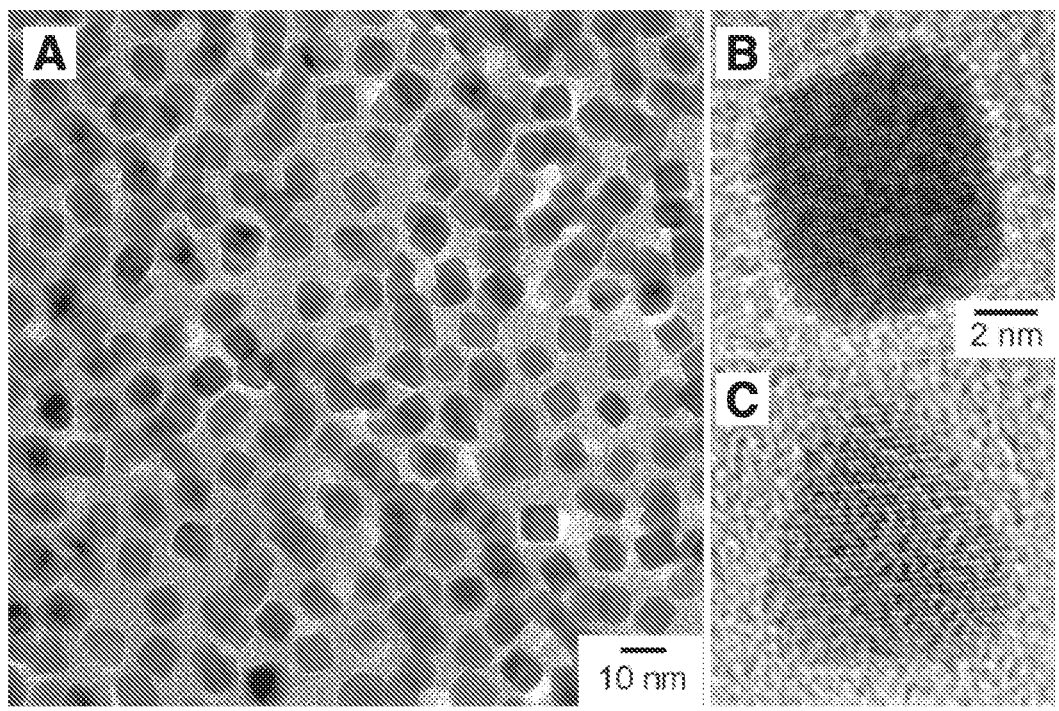

FIG. 22A-C are images of Pt cubes according to the present invention, wherein FIG. 22A is a TEM image of Pt cubes, FIG. 22B is an HRTEM image of the Pt cube along the [001] zone axis, and FIG. 22C is an HRTEM image of the Pt tetrahedron along the [111] zone axis.

Figure 23:
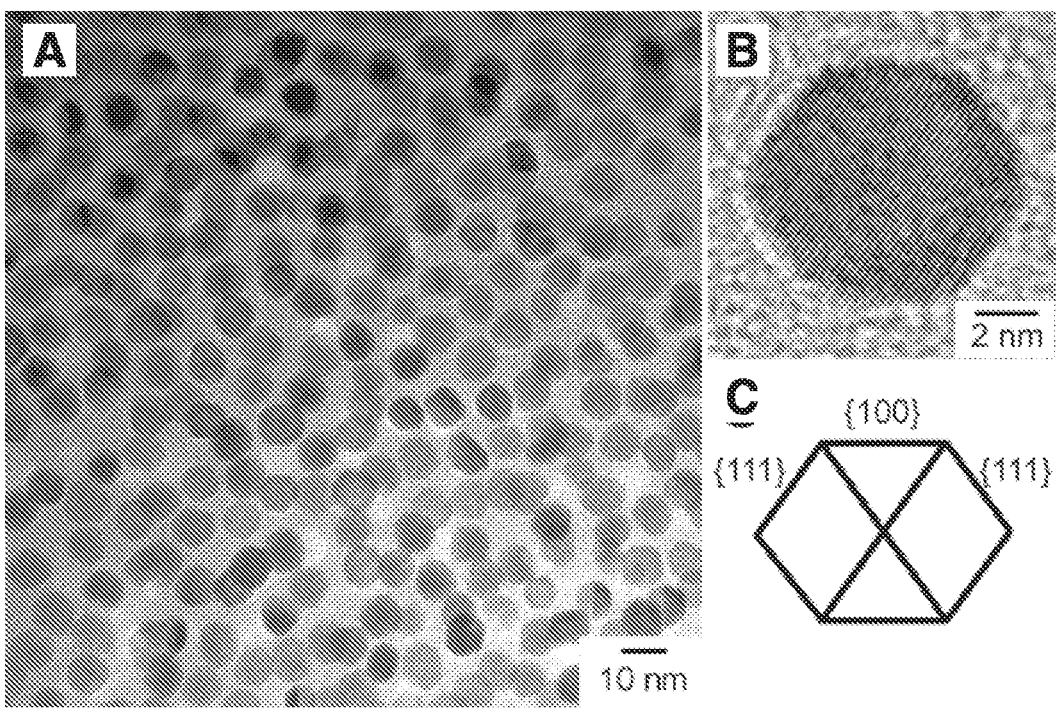

FIG. 23A-C are images of cuboctahedra according to the present invention, wherein FIG. 23A is a TEM image of Pt cuboctahedra, FIG. 23B is an HRTEM image of the Pt cuboctahedron along the [110] zone axis, and FIG. 23C is a 2D projection of an ideal cuboctahedron along the [110] direction.

Figure 24:
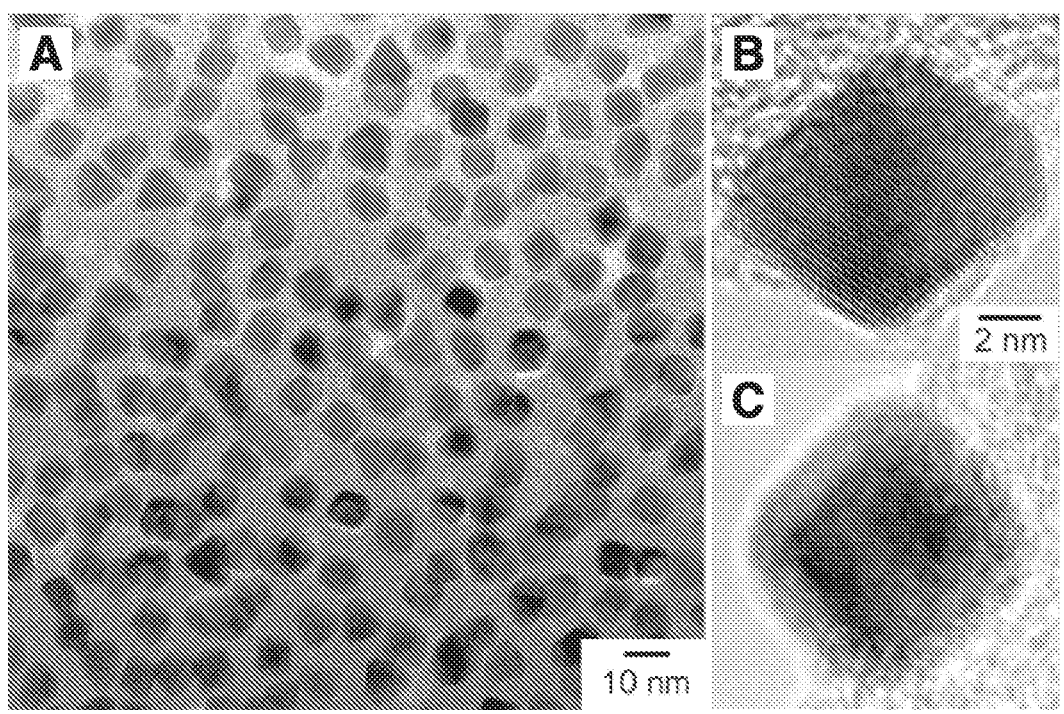

FIG. 24A-C are images of Pt octahedra according to the invention wherein FIG. 24A is a TEM image of Pt octahedral, FIG. 24B is an HRTEM image of the Pt octahedron along the [110] zone axis, and FIG. 24C is an HRTEM image of the Pt octahedron along the [001] zone axis.

Figure 25:
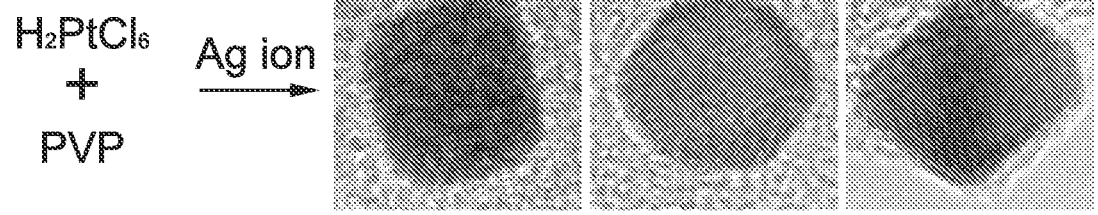

FIG. 25 is a flow diagram illustrating a generalization of the modified polyol process according to the invention.

Figure 26A:
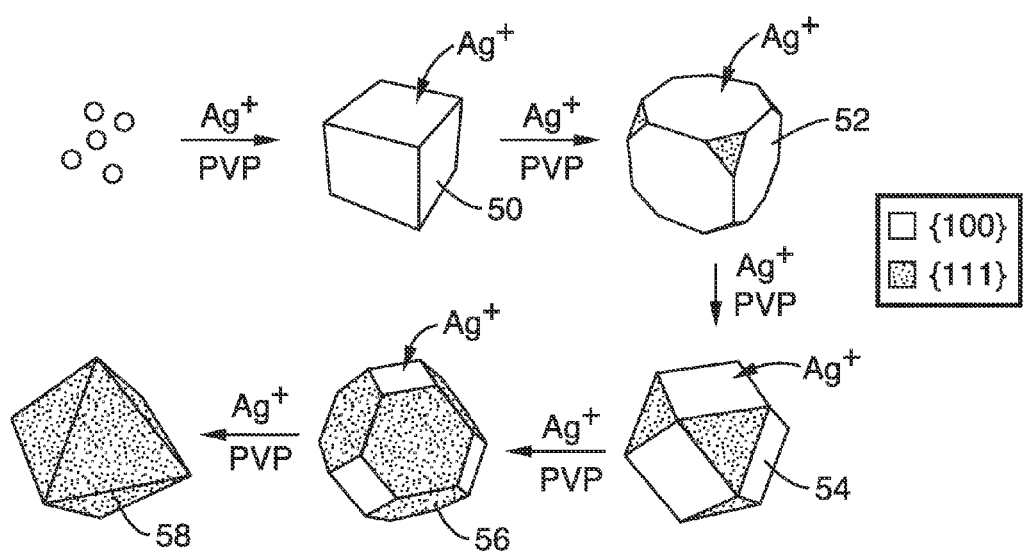
Figure 26B:
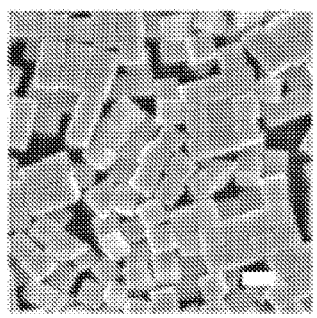
Figure 26C:
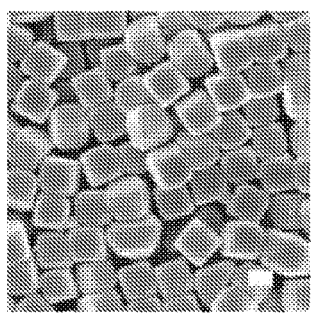
Figure 26D:
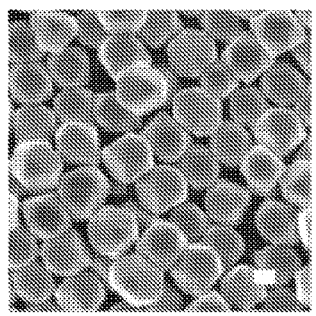
Figure 26E:
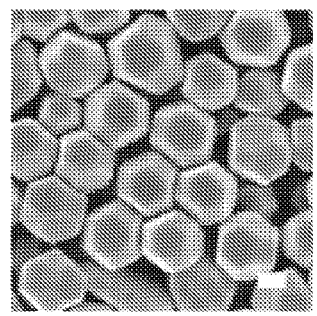
Figure 26F:
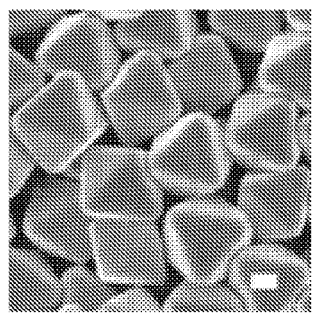

FIG. 26A illustrates a schematic diagram of the nucleation and growth process of polyhedral nanocrystals.

FIGS. 26B-F are SEM images of cubes, truncated cubes, cuboctahedra, truncated octahedra, and octahedra, respectively.

Figure 27:
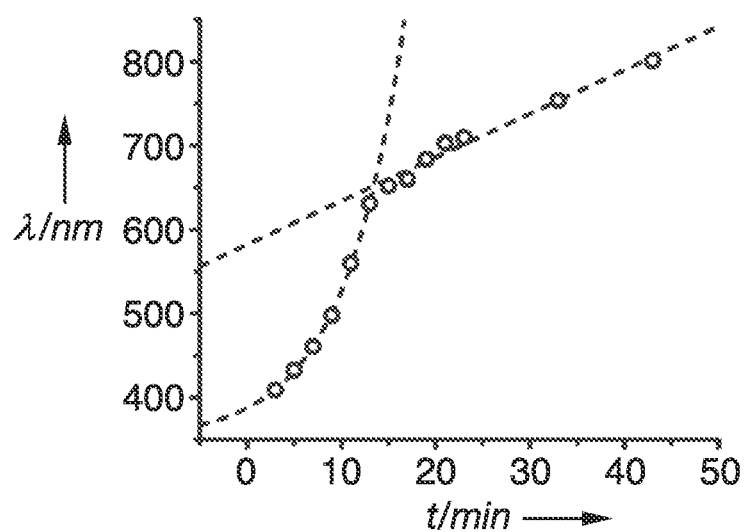

FIG. 27 is a plot of reaction time versus dipolar surface plasmon wavelength.

Figure 28A:
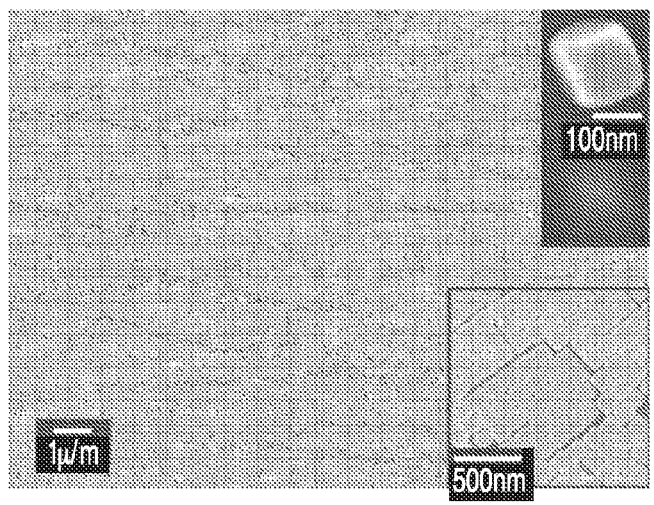
Figure 28B:
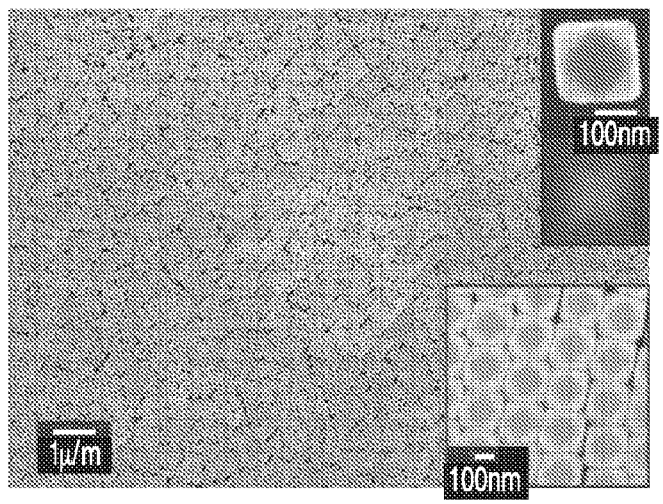
Figure 28C:
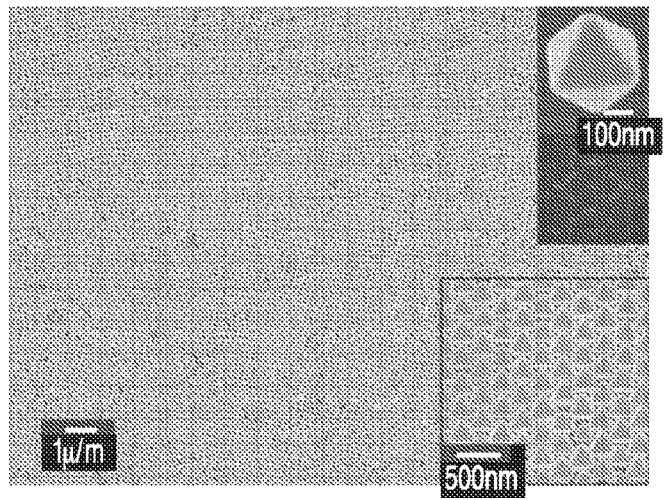

FIGS. 28A-C show SEM images of close-packed NC monolayers obtained after isothermal compression of an LB NC.

Figure 29A:
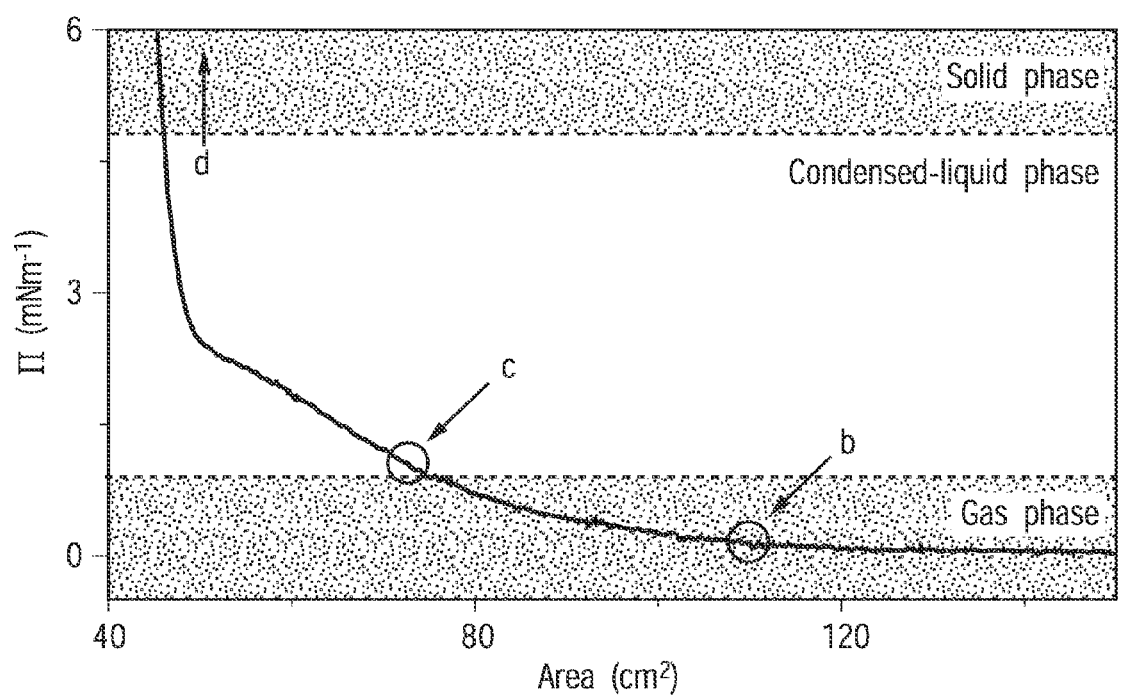

FIG. 29A shows a typical pressure-area isotherm for an LB compression.

Figure 29B:
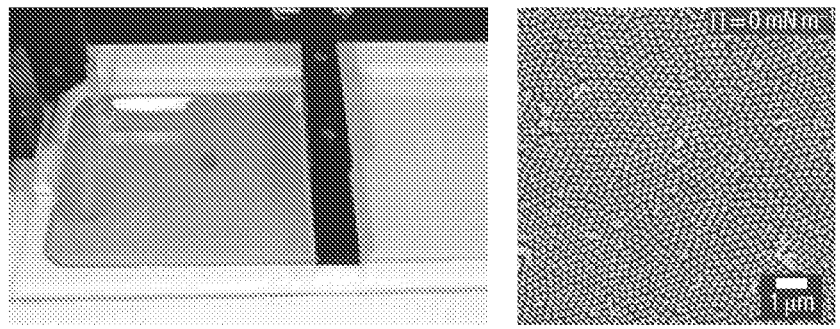
Figure 29C:
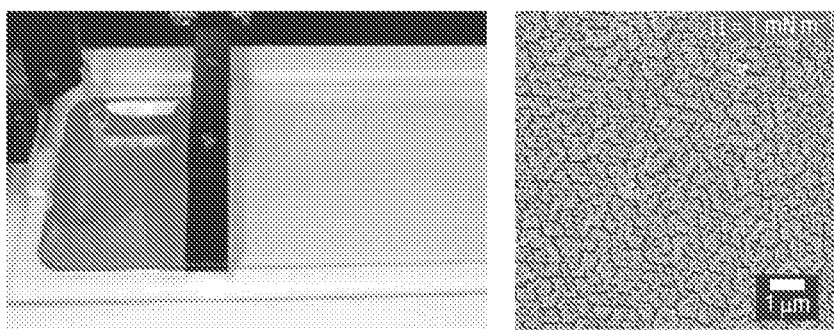
Figure 29D:
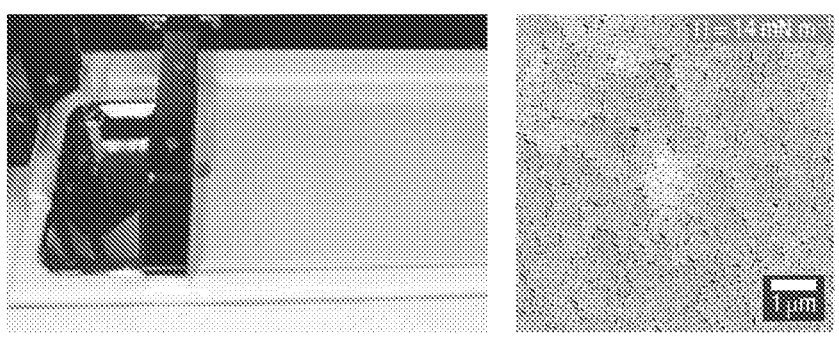

FIGS. 29B-D are photos of the fluid-supported NC film and corresponding SEM images of film after transfer to a Si substrate during isothermal compression.

Figure 30A:
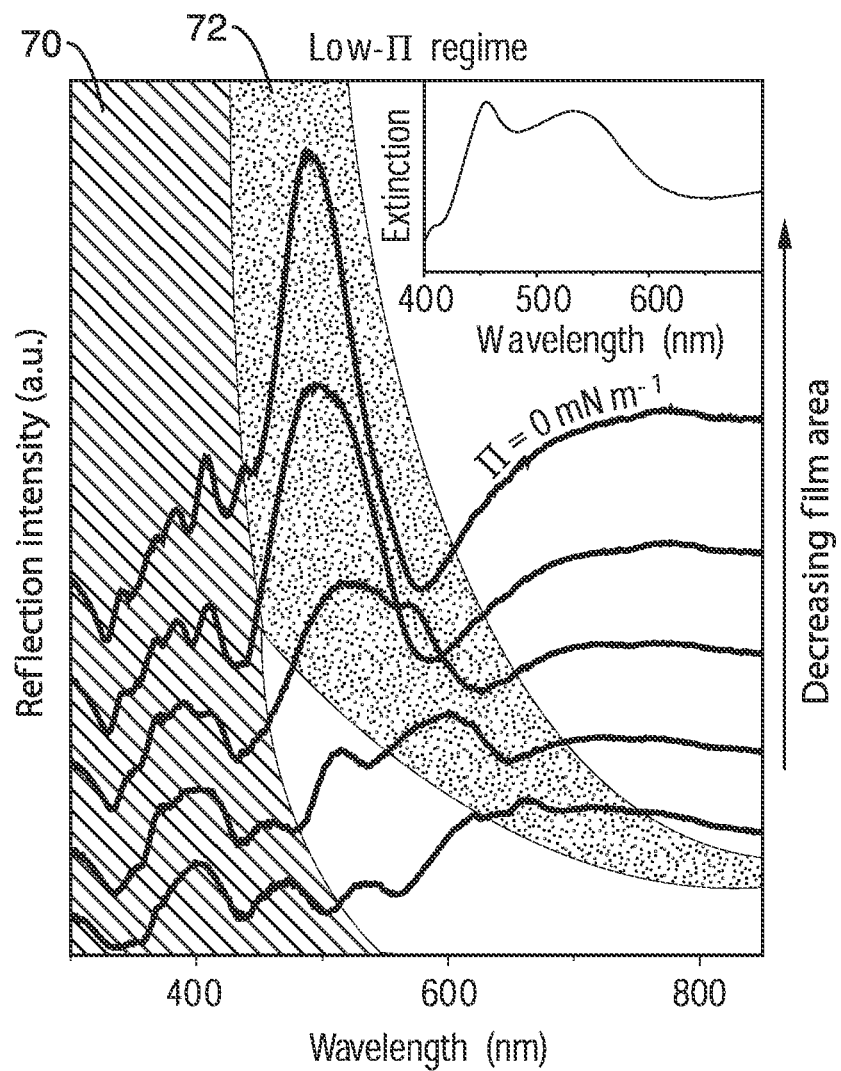
Figure 30B:
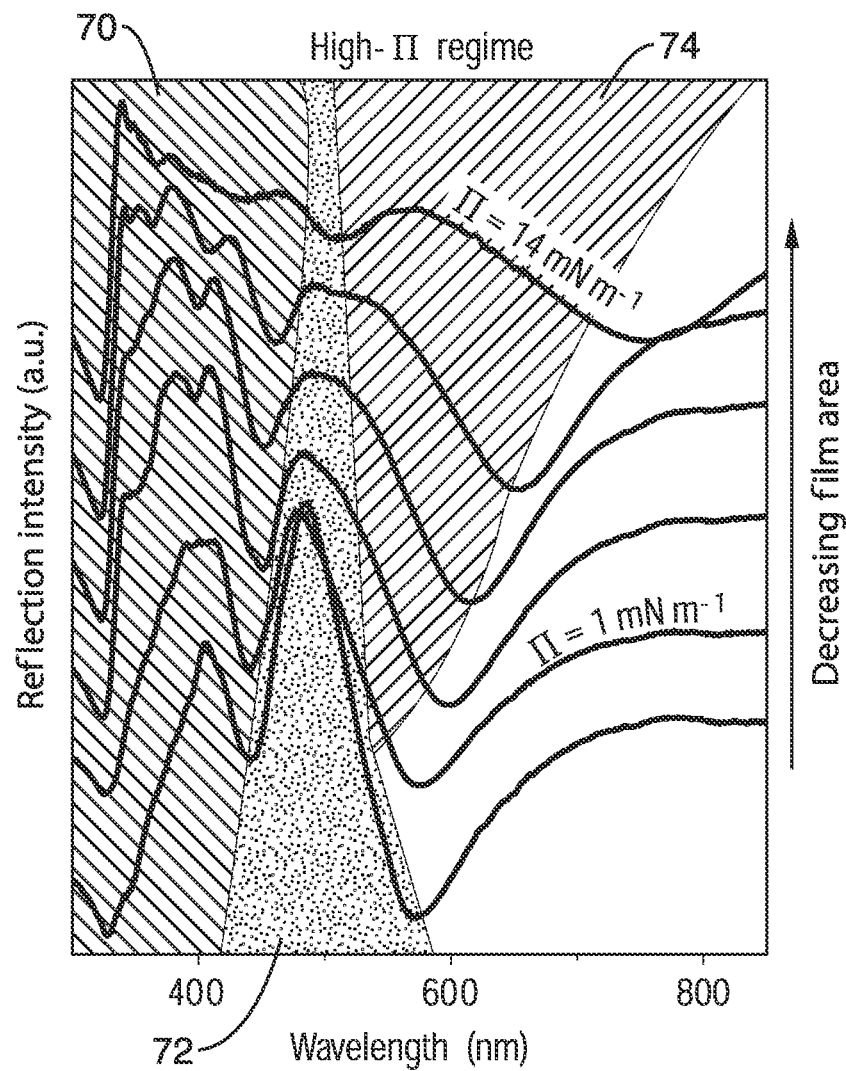
Figure 30C:
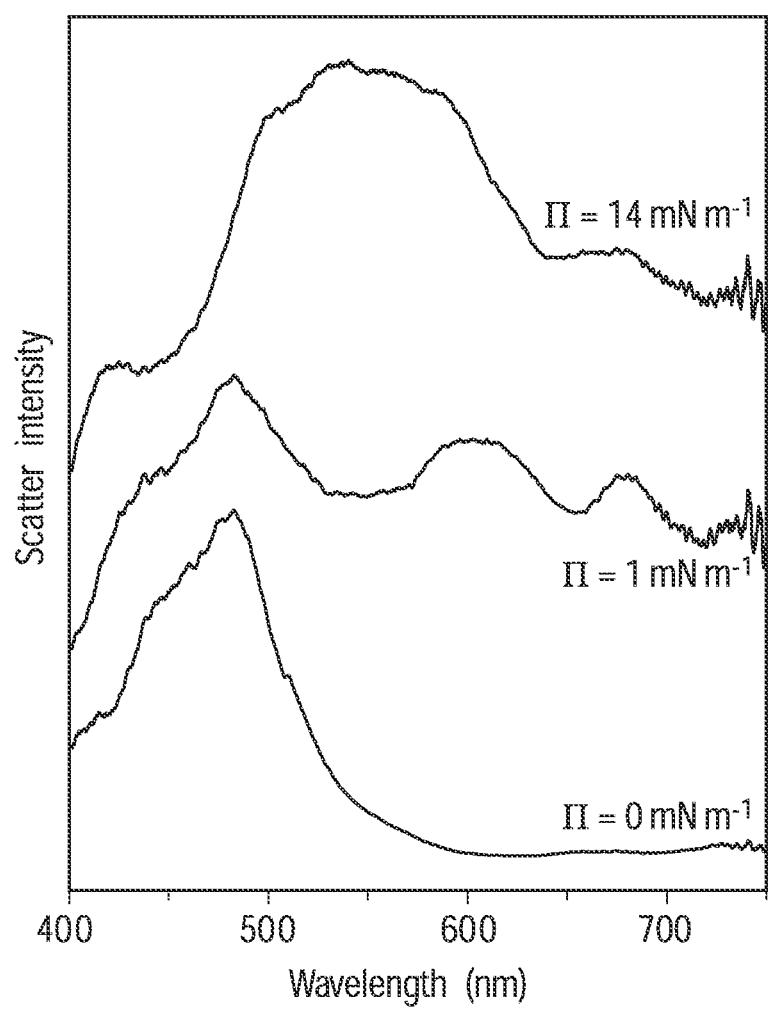
Figure 30D:
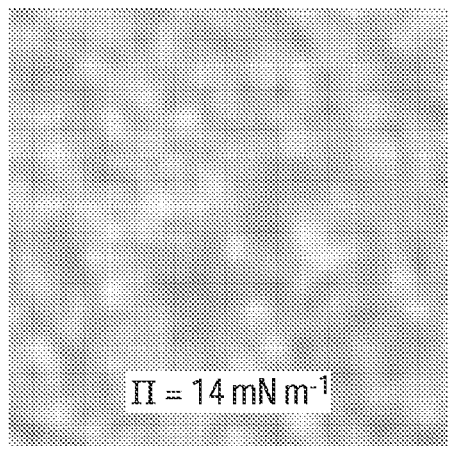

FIGS. 30A-B show specular reflectance measurements obtained in situ at the air-water interface during the initial stages of monolayer compression Spectra are offset for clarity FIG. 30C shows dark-field scattering spectra for the NC monolayers at the indicated surface pressures.

Figure 30E:
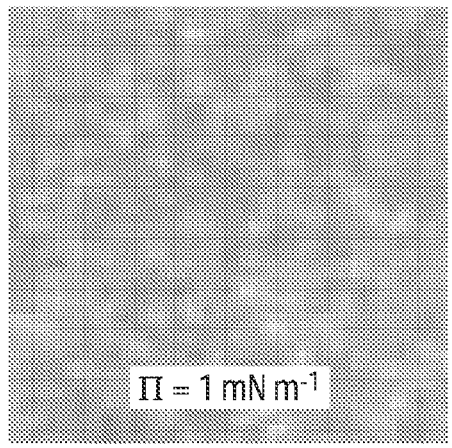
Figure 30F:
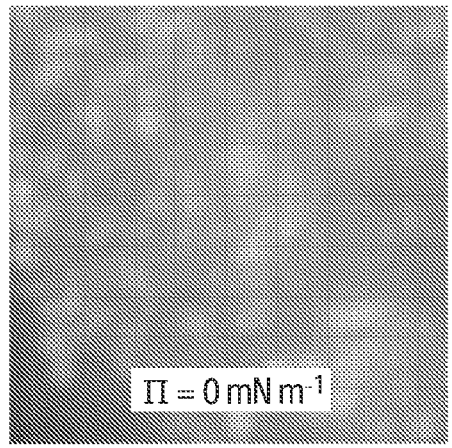

FIGS. 30E-F show digital images of each film (in FIGS. 29B-D) under dark-field illumination.

Figure 31A:
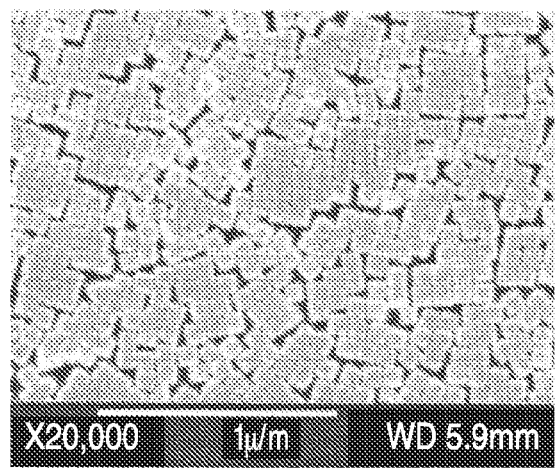
Figure 31B:
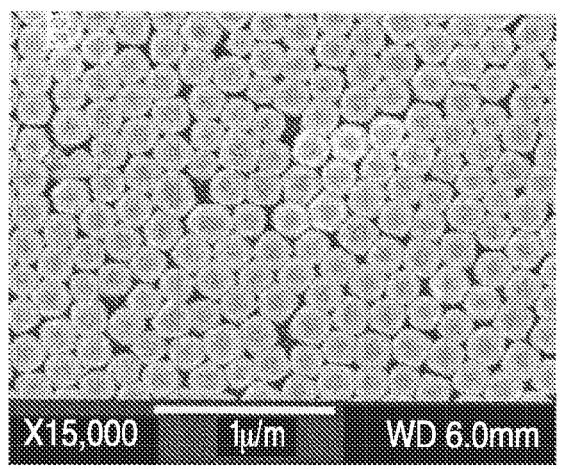
Figure 31C:
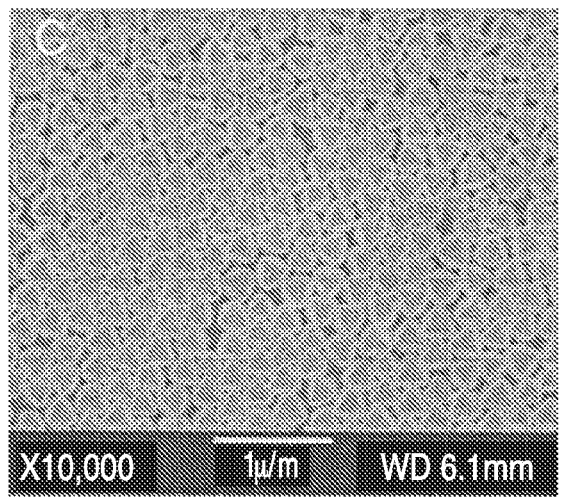
Figure 32A:
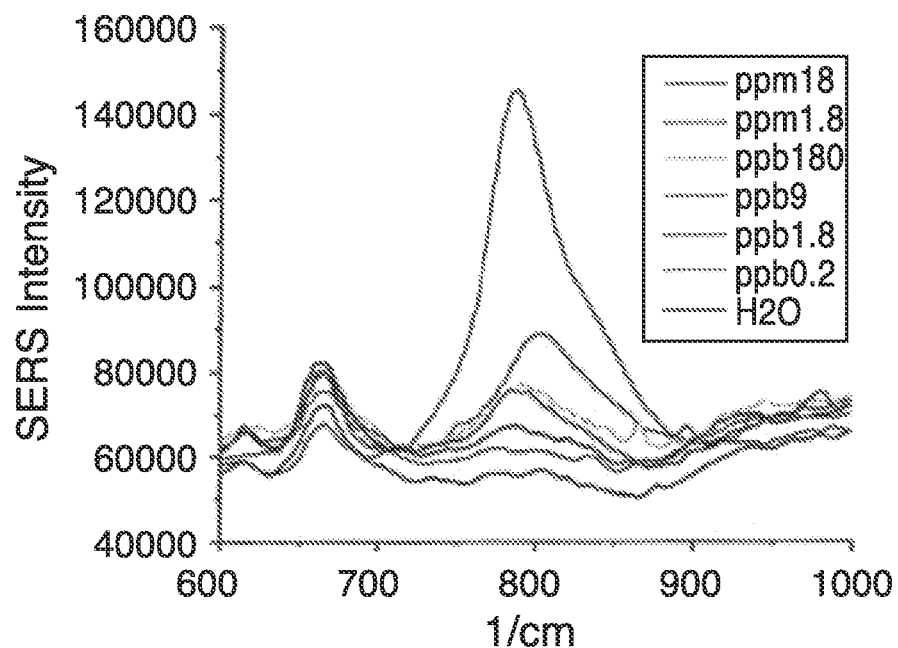
Figure 32B:
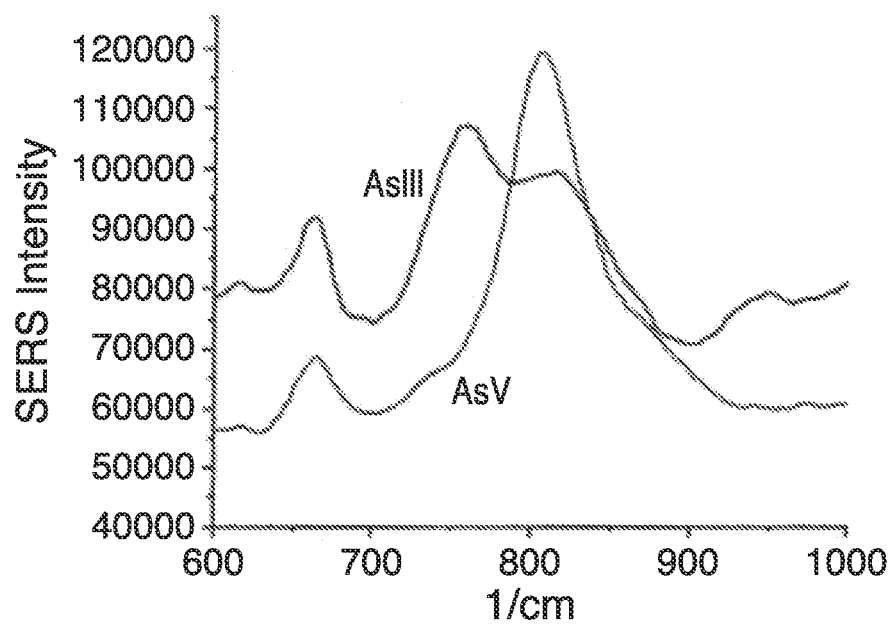

FIGS. 31A-C show SEM images of silver shapes after Langmuir Blodgett assembly according to the present invention FIGS. 32A-B show the results of surface enhanced Raman spectroscopy on silver octahedra films.

Figure 33:
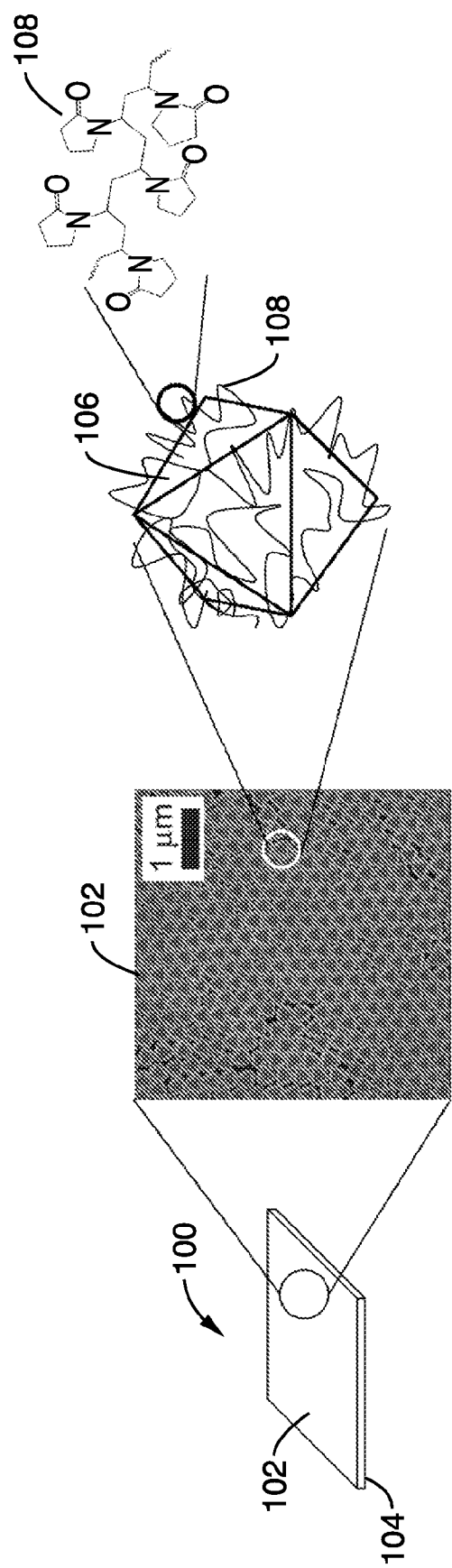

FIG. 33 is a schematic diagram of the structure of a SERS substrate sensor in accordance with the present invention.

DETAILED DESCRIPTION OF THE INVENTION

Figure 1:
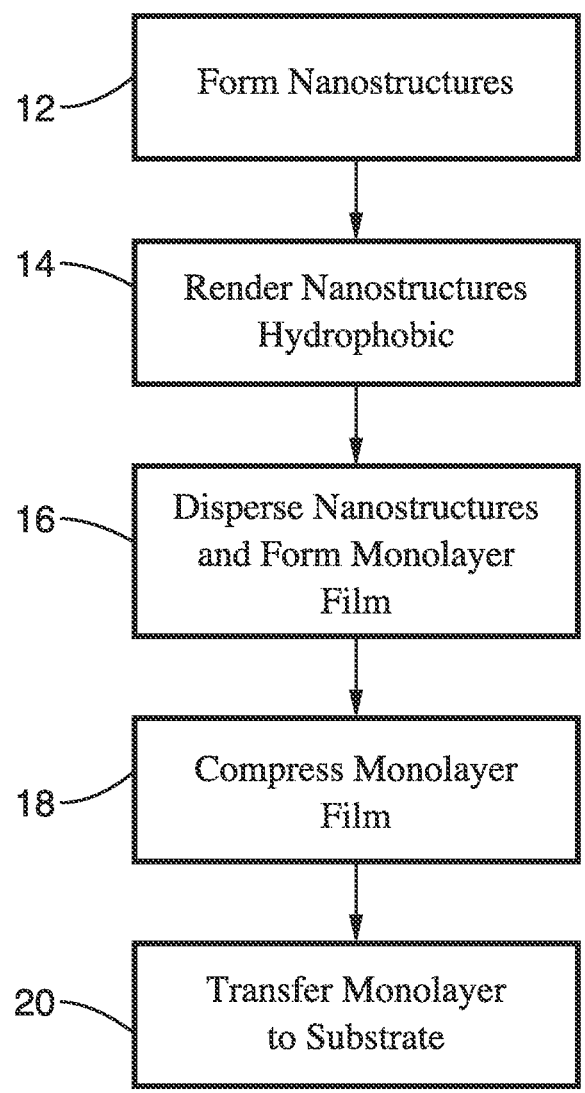

The present invention generally comprises methods for fabricating a monolayer of nanostructures and assemblies and devices therefrom. By way of example, and not of limitation, an embodiment of the fabrication method is illustrated in FIG. 1. In the exemplary embodiment shown in FIG. 1, a plurality of nanostructures is formed a step 12. After the nanostructures are formed, they are rendered hydrophobic at step 14. At step 16, the nanostructures are then dispersed onto a water surface of a Langmuir-Blodgett (LB) trough and a monolayer of ordered nanostructures is formed. The monolayer is then compressed at step 18, and transferred to a substrate at step 20.

It will be appreciated that, during the formation step 12, the nanostructures can be formed with various lengths and cross-sectional shapes. The resultant nanostructures can have shapes that include, but are not limited to, cubic, plate-shaped, rod-shaped, triangular, pentagonal and hexagonal. In one beneficial embodiment for use as sensors, the nanostructures can be nanowires having diameters of up to approximately 50 nm and pyramidal tips with vertices as sharp as 2 nm. The size of the monolayer can be varied, and areas exceeding approximately 20 $cm^2$ are achievable. The transfer step 20 can comprise, for example, depositing the compressed monolayer onto the surface of a substrate such as silicon, glass, polymer or other material, or embedding the monolayer into a polymer material such as polydimethylsiloxane (PDMS). The resultant monolayers are suitable for use in surface enhanced Raman spectroscopy (SERS), for molecular-specific sensing using vibrational signatures, as interconnects, and as wire-grid optical polarizers. Assemblies and devices can be formed by placing the monolayer into multilayer structures.

In another beneficial embodiment, the nanostructures are silver nanowires formed using a solution-phase polyol process wherein the nanowires have faceted cross-sections. In this embodiment, a monolayer film is formed in step 16 where the nanowires exhibit substantial parallel alignment. During the compression step 18 the monolayer is formed through an insulator-to-metal transition. Nanowires are close-packed as parallel arrays with their longitudinal axes aligned perpendicular to the compression direction.

EXAMPLE 1

Assembling Aligned Monolayers

In the following discussion, we report our success with utilizing the foregoing processes to assemble aligned monolayers (with area over 20 $cm^2$) of silver nanowires that are ~50 nm in diameter and 2-3 micrometers in length. These nanowires (characterized by pentagonal cross-sections and pyramidal tips) were close-packed as parallel arrays, with their longitudinal axes aligned perpendicular to the compression direction. The resulting nanowire monolayers can serve as good surface enhanced Raman Spectroscopy substrates, exhibit large electromagnetic field enhancement factors ($2 \times 10^5$ for thiol and 2,4-dinitrotoluene, $2 \times 10^9$ for Rhodamine 6G) and can readily be used in ultrasensitive, molecular-specific sensing utilizing vibrational signatures.

Figure 2:
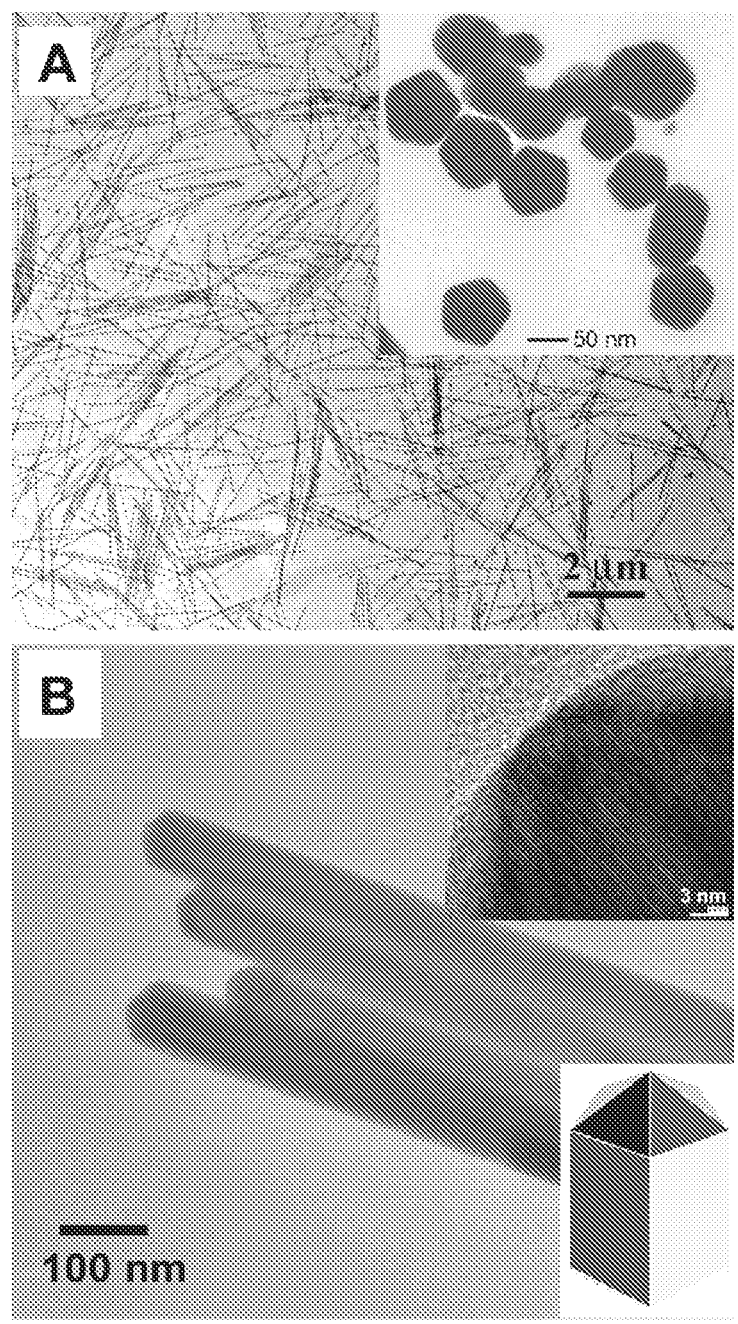

Silver nanowires were prepared using poly(vinyl pyrrolidone) (PVP) as the capping agent. The as-prepared samples were purified to remove spherical nanoparticles. The resulting nanowires were uniform in both diameter (45.3±3.6 nm) and aspect ratio (45±5). After functionalizing with 1-hexadecanethiol ligands, the wires were rendered hydrophobic and re-dispersed in chloroform FIGS. 2A and B are transmission electron microscopy images of the uniform Ag nanowires before the LB assembly. The inset in FIG. 2A is an image taken from a microtomed sample, showing the pentagonal cross-sections of the nanowires. A high resolution TEM image, the upper inset in FIG. 2B, shows the sharp pentagonal pyramidal tip of a silver nanowire, as schematically illustrated in the bottom inset in FIG. 2B. An important feature of these nanowires was their pentagonal cross-sections, as shown in the inset of FIG. 2A. In addition, these wires possessed pentagonal pyramidal ends with vertices as sharp as 2 nm as shown in the lower inset of FIG. 2B. The non-circular cross-sections and sharp wire tips potentially have important consequence for molecular sensing using surface enhanced Raman spectroscopy (SERS). The nanowires were then dispersed onto a water surface of the Langmuir-Blodgett trough. It is important to note that the displacement of the PVP capping agents with thiol ligands was required to render the nanowire surface hydrophobic as well as to prevent aggregation.

Figure 3:
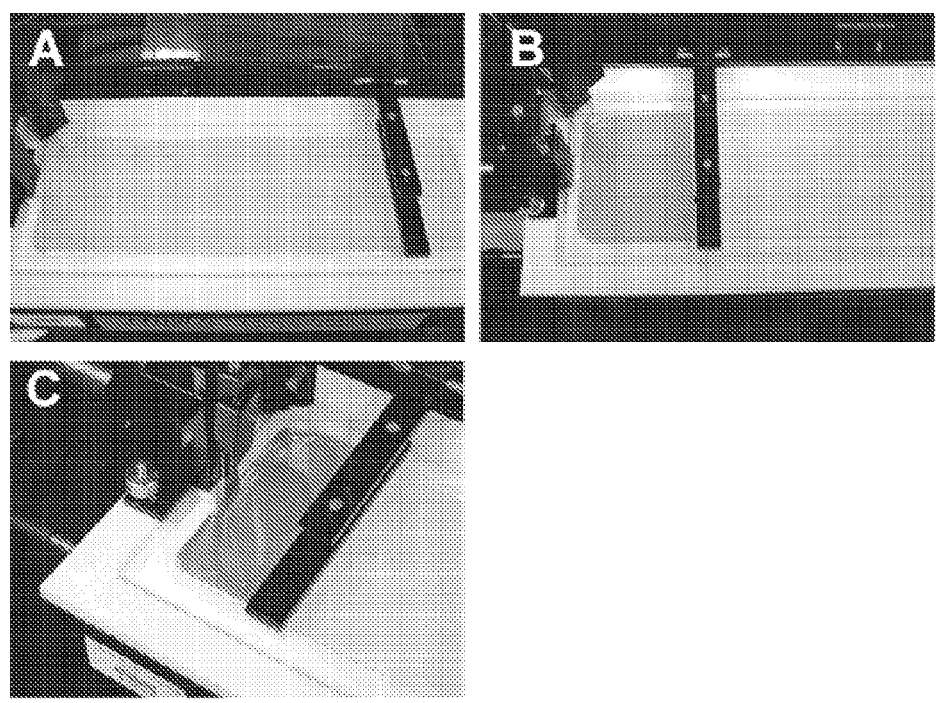
Figure 4:
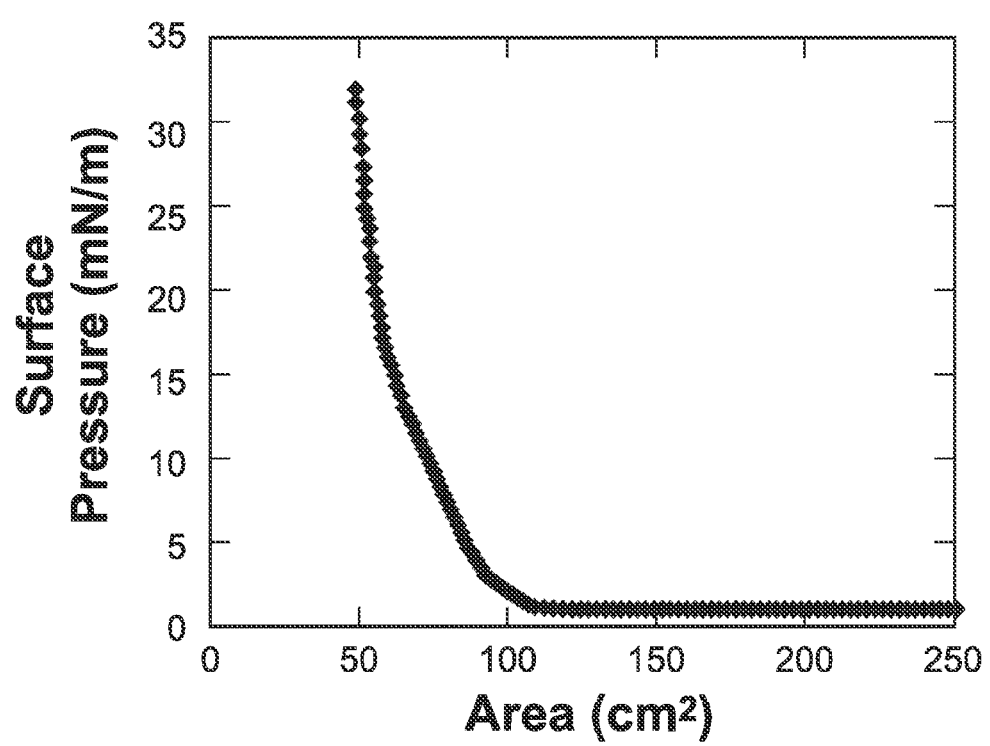
Figure 5:
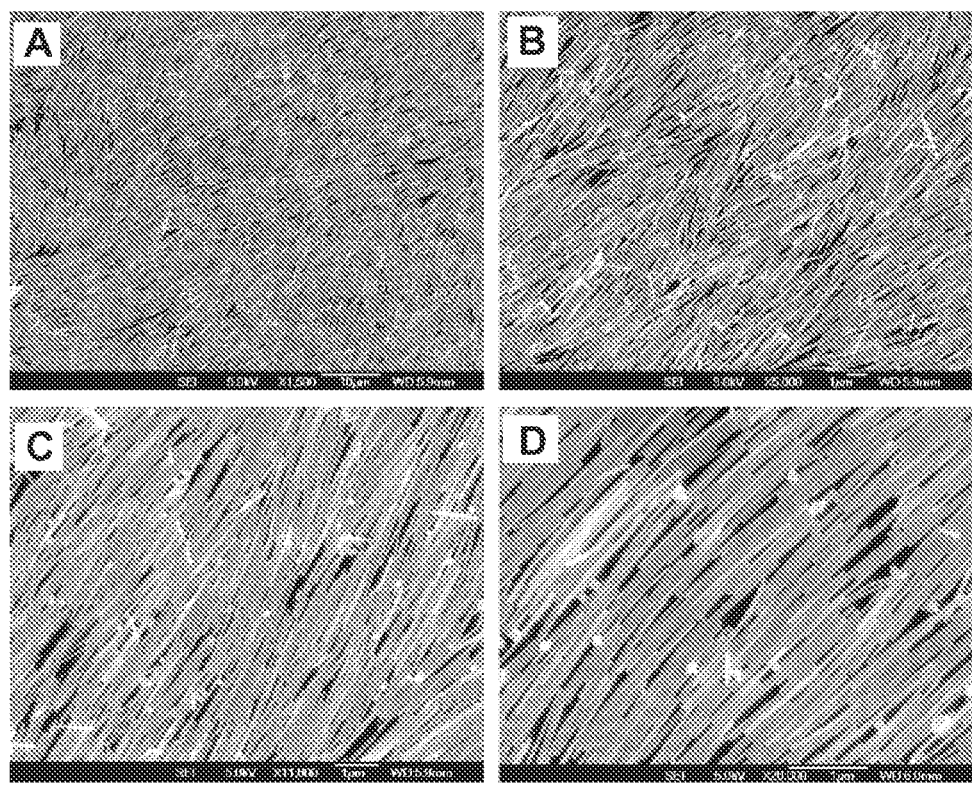

The assembly process was effectively a microscopic version of "logs-on-a-river". FIG. 3A through C are photographs showing the LB nanowire assembly process at different progressive compression stages. FIG. 4 is a surface pressure curve recorded during the assembly process illustrated in FIG. 3. FIG. 3A shows the nanowires dispersed on a trough water surface. At this stage, the surface pressure was zero (see FIG. 4), the nanowires were randomly oriented, and the water surface was essentially transparent. The monolayer was then compressed. When the nanowires were compressed, the surface pressure increased (FIG. 3B, FIG. 4). Above 14 mN/m, the monolayer underwent a Mott-insulator-to-metal transition, as previously seen in Langmuir-Blodgett monolayers of spherical Ag nanocrystals. This transition was indicated by the appearance of a metallic sheen on the nanowire monolayer surface. FIG. 3C shows the monolayer in its highly-reflective metallic state. This particular sample covered a trough area of 20 cm². However, the final aligned area is limited only by the amount of initial material used for the compression. Therefore, it is possible to prepare these monolayers on any substrate over an arbitrarily large area.

Significantly, the compressed silver nanowire monolayer exhibited remarkable alignment parallel to the trough barrier. FIG. 5A-D show scanning electron microscopy (SEM) images at different magnifications of the solver nanowire monolayer transferred onto a silicon wafer. As can be seen, the nanowires are aligned side-by-side over large areas, resembling a nematic 2-dimensional ordering of a liquid crystal. This large-scale directional ordering was also verified by imaging the sample under an optical microscope equipped with a set of cross-polarizers. The aligned nanowire domains displayed alternating extinction patterns when the sample was rotated every forty-five degrees.

Figure 6:
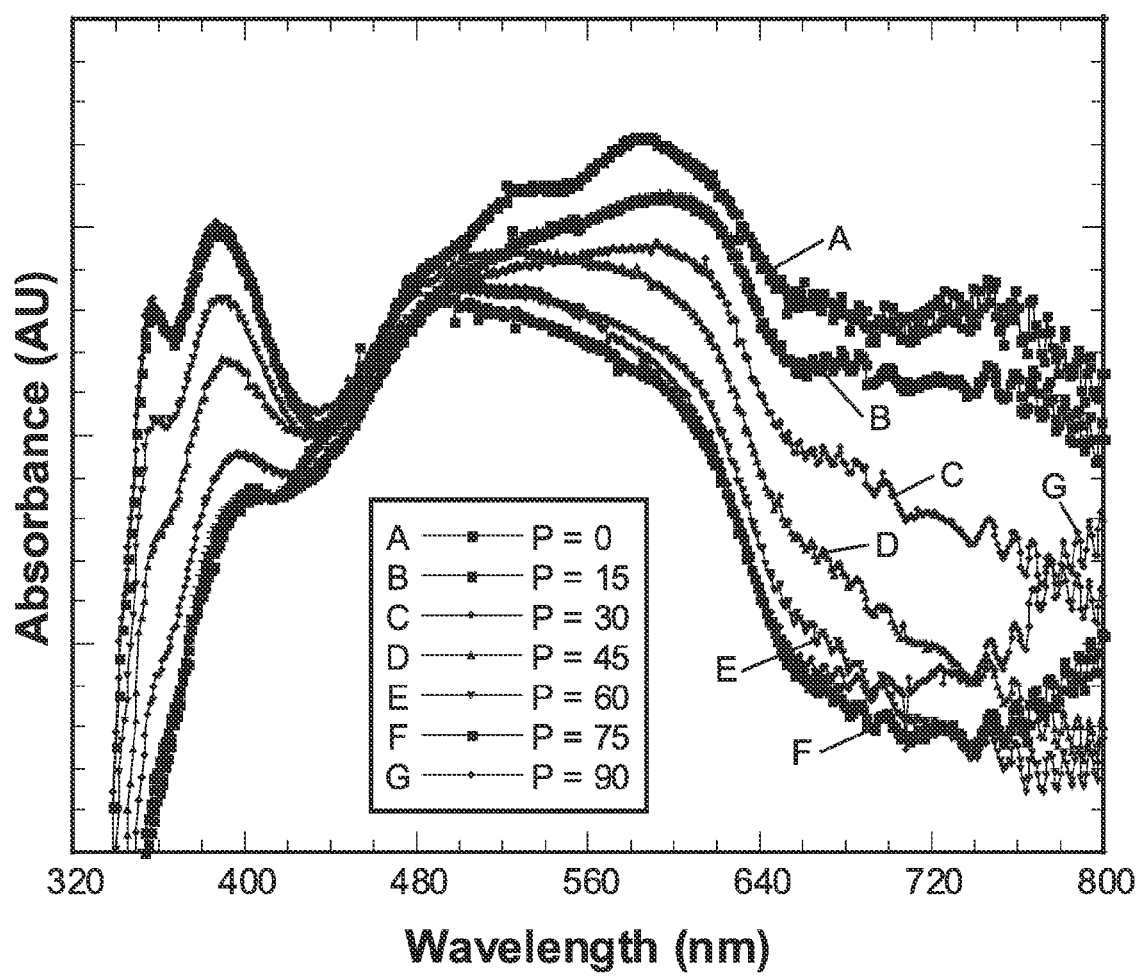
FIG. 6 illustrates the UV-VIS absorption spectra of a silver nanowire monolayer assembled according to an embodiment of the present invention. All spectra were obtained at normal incidence with the polarization angles (P) defined as θ=0°, when the incident electric field is parallel to the direction of nanowire alignment and θ=90° when the filed is perpendicular to the nanowire axis.

The dependence of the extinction spectra as a function of the polarization angle of the input optical beam was recorded with a polarized UV-VIS spectrometer. FIG. 6 shows a typical set of UV-VIS spectra or the silver nanowire monolayer at different polarization angles. All spectra were obtained at normal incidence with the polarization angles (P) defined as $\theta=0°$, when the incident electric field is parallel to the direction of nanowire alignment and $\theta=90°$ when the filed is perpendicular to the nanowire axis. Note that strong optical dichroism can be seen in these spectra. Three sets of peaks were observed: 350 nm, 380 nm, and a broad peak at 500-700 nm. When the polarization of the incident light was perpendicular to the wire axis, the transverse mode of the surface plasma experienced preferred excitation; as a result, the 380 nm extinction peak exhibited the highest intensity with this configuration. When the polarization angle was increased from zero degrees (normal to wire axis) to ninety degrees (parallel to wire axis), the intensity for the 500-600 nm peaks increased. This extinction peak can be attributed to the excitation of longitudinal plasma within the monolayer. The significant broadening is believed to stem from the coupling of electromagnetic waves among neighboring nanowires.

Significantly, this large area of nanowire alignment observed enables the fabrication of high density nanoscale interconnects and sensor arrays, as well as multilayer structures via a layer-by-layer transfer approach. These monolayers can be readily transferred to any desired substrates, including silicon wafers, glass slides, and polymer and other substrates. For example, we have successfully embedded monolayers and multilayers of these silver nanowires within polydimethylsiloxane (PDMS), giving flexible nanowire-polymer composites that can serve as simple wire-grid optical polarizers. Thus, the present invention is a very powerful technique for the organization of anisotropic building blocks into functional nanoscale assemblies with unprecedented high packing density.

Figure 7:
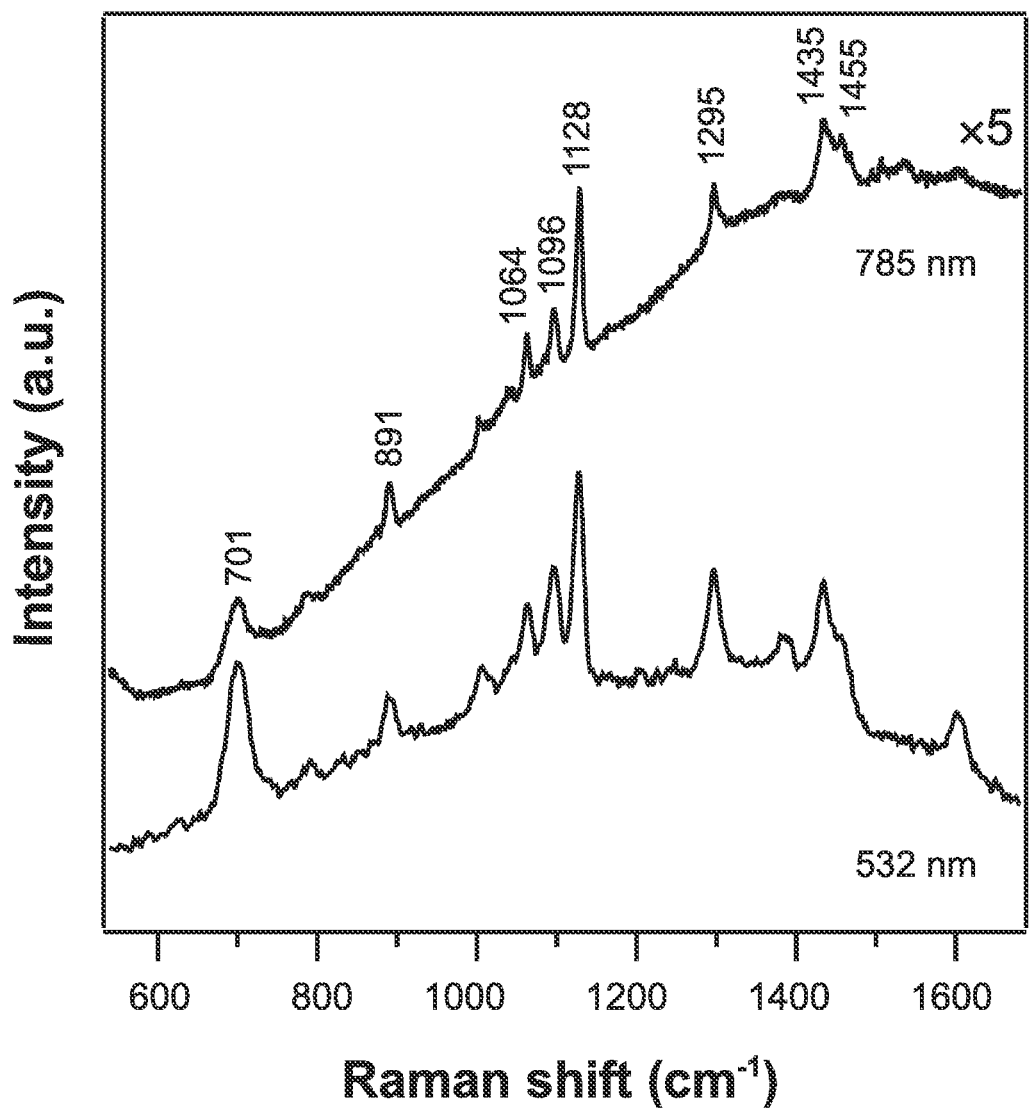
FIG. 7 is a graph illustrating surface-enhanced Raman spectroscopy on a silver nanowire monolayer assembled according to an embodiment of the invention, showing SERS spectra of 1-hexadecanethiol on a Langmuir-Blodgett film of silver nanowires with visible (532 nm, 25 mW) and near-infrared excitation (785 nm, 10 mW).

It is also significant that these aligned nanowire monolayers can be readily used as surface-enhanced Raman spectroscopy (SERS) substrates for molecular sensing with high sensitivity and specificity. These metallic layers are expected to exhibit giant local electromagnetic (EM) field enhancement, particularly for nanowires with sharp tips and non-circular cross-sections (as in the example described above, a pentagonal cross-section). FIG. 7 shows the SERS spectrum of 1-hexadecanethiol on a Langmuir-Blodgett film of silver nanowires for visible (532 nm, 25 mW) and near-infrared excitation (785 nm, 10 mW). The observed bands were characteristic of 1-hexadecanethiol. The Raman bands in the low-frequency part of the spectrum include: the $v(C-S)_{trans}$ at 701 cm$^{-1}$; the CH$_3$ rocking mode at 891 cm$^{-1}$; the $v(C-C)$ at 1064, 1096, and 1128 cm$^{-1}$; the CH$_2$ wag at 1295 cm$^{-1}$; the CH$_2$ twist at 1435 cm$^{-1}$; and the CH$_2$ scissor at 1455 cm$^{-1}$. The $v(C-S)_{trans}$ at 701 cm$^{-1}$ is indicative of well-ordered alkyl chains with largely trans conformation near the thiol head-group. In the C-C region, the presence of an intense 1128 cm$^{-1}$ and a weaker 1096 cm$^{-1}$ neighbor (indicative of trans bonding) suggests that the adsorbed thiol possesses a "solid-like" structure extending beyond the surface region into the hydrocarbon tail.

The enhancement factor (EF) for 1-hexadecanethiol/Ag was calculated according to the following expression:

$$EF=[I_{SERS}]/[I_{Raman}]\times[M_b]/[M_{ads}]$$

where $M_b$ is the concentration of molecules in the bulk sample, $M_{ads}$ is the concentration of adsorbed molecules, and $I_{SERS}$ and $I_{Raman}$ are intensities in the SER and Raman spectrum, respectively. The concentration of adsorbed molecules was estimated by dividing the total surface area of a single nanowire by the van der Waals dimensions (2.3 Å×2.3 Å) of the thiol head group. Assuming 1-hexadecanethiol forms a close-packed monolayer perpendicular to the surface, the number of adsorbed molecules was calculated to be 2.5×10$^{14}$/cm$^2$. Intensities were compared to the Raman scattering of a 0.1 M 1-hexadecanethiol solution. For the vibration mode at 1295 cm$^{-1}$, an EF of 2×10$^5$ was obtained. Values of similar magnitude have been observed on other SERS-active Ag substrates at optimum visible excitation wavelengths. This enhancement can be attributed to increased local optical fields near the Ag surface due to the excitation of surface plasmon resonances.

Interestingly, near-infrared excitation (785 nm) of 1-hexadecanethiol/Ag gave rise to comparable SERS intensities. We believe this effect stems from the interaction of individual Ag wires within the film. In the absorption spectrum of an LB film, a broad resonance evolves from this interaction, giving a peak around 550 nm that extends into the near-infrared region. Thus, LB nanowire films should serve as extremely versatile SERS substrates, allowing excitation over a wide range of frequencies.

Figure 8:
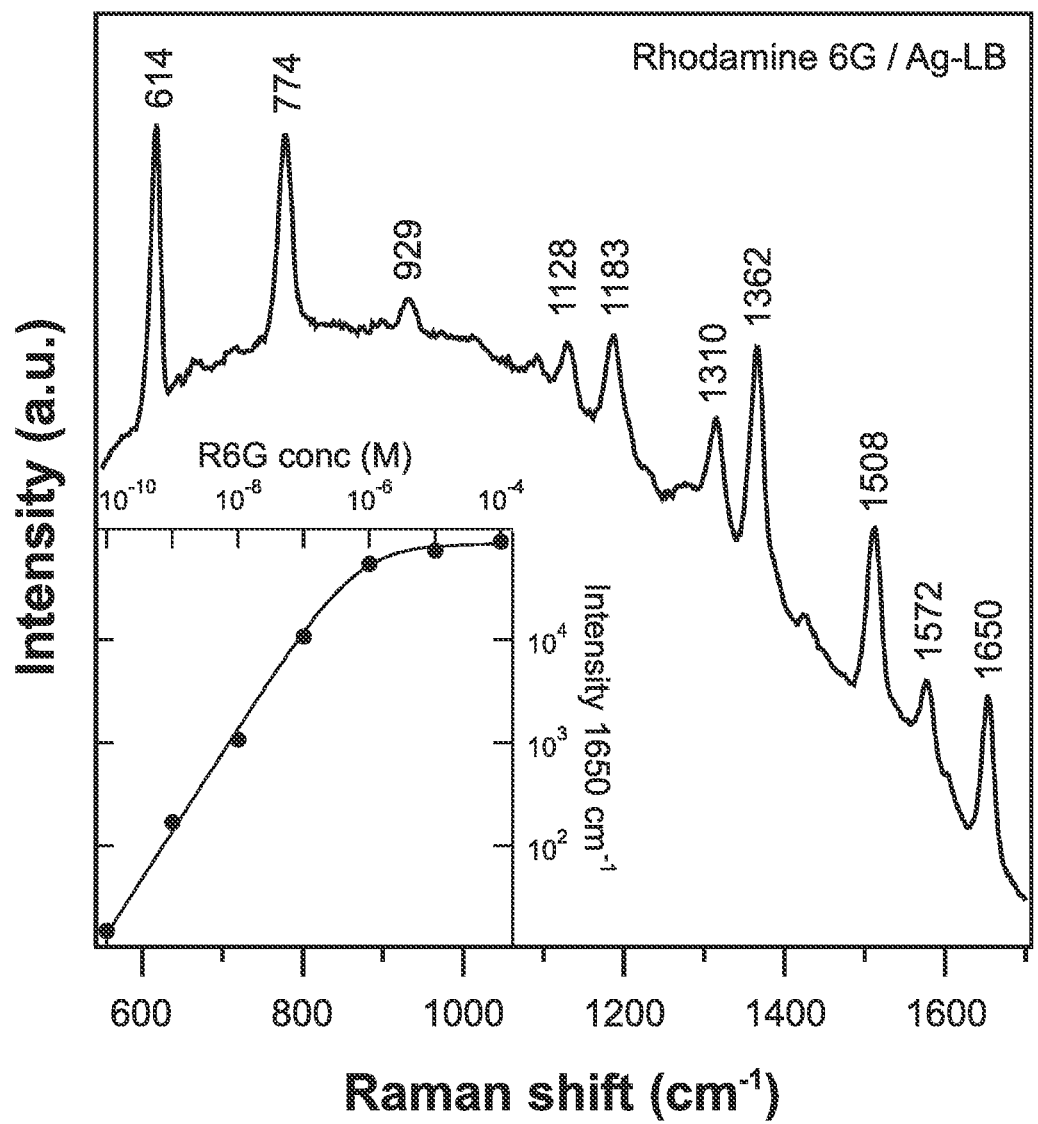
FIG. 8 is a graph illustrating surface-enhanced Raman spectroscopy on a silver nanowire monolayer assembled according to an embodiment of the invention, showing SERS spectrum of R6G on the thiol-capped Ag-LB film (532 nm, 25 mW) after 10 min incubation in a $10^{-9}$ M R6G solution. The inset shows the linear relationship between the Raman intensity ($I_{SERS, 1650}$) and the R6G concentration.

Rhodamine 6G (R6G) is a strongly fluorescent xanthene derivative which shows a molecular resonance Raman (RR) effect when excited with 25 mW at 532 nm. FIG. 8 depicts the SERS spectrum of R6G on a thiol-covered LB film after a 10-minute incubation in a $10^{-9}$ M R6G solution. The quenching of the fluorescence and huge SERS enhancement factor indicate that the R6G molecules spontaneously adsorb on the Ag nanowires. In addition, a linear relationship between Raman intensity ($I_{SERS,\ 1650}$) and R6G concentration was observed as shown in the inset of FIG. 8. A least-square fit of the data (solid line in inset) using a Langmuir adsorption isotherm gives an adsorption energy of 46 kJ/mol, which suggests that R6G has strong interaction with the surface of the wires. More importantly, these observations show that despite the presence of thiol capping agents, the surface of the Ag nanowire film offers free sites which allow for the adsorption and therefore identification of any unknown analyte. Based on the field enhancement factor obtained for the thiol and the fact that the ratio of the Raman intensities of the R6G- and thiol-related C-C stretching bands at R6G saturation coverage is ~$10^4$, the EF for R6G is estimated to be $2 \times 10^9$.

The observed large enhancement factors suggest that these monolayers can indeed serve as robust solid substrates for carrying out molecular sensing with high sensitivity and specificity (as SERS readily reveals the vibrational signature of an analyte). Here we demonstrate the capability of our nanowire substrates for the detection of 2,4-dinitrotoluene (2,4-DNT), the most common nitroaromatic compound for detecting buried landmines and other explosives. SERS from 2,4-DNT has been obtained previously. FIG. 9 shows a SERS spectrum of 2,4-DNT on the thiol-capped Ag nanowire monolayers after incubation for 10 min in $10^{-2}$ M 2,4-DNT/MeOH solution. The spectrum was recorded using 25 mW of 532 nm laser light. The acquisition time was 10 s. The $NO_2$ stretching mode at 1348 $cm^{-1}$, which is the key vibrational mode for the analysis of 2,4-DNT, is clearly displayed and well-separated from the surfactant-related Raman bands at 1295 and 1435 $cm^{-1}$. We achieved a sensitivity of approximately 0.7 pg, assuming a monolayer coverage for 2,4-DNT and an area of 45 $Å^2$ per adsorbate. Based on the same assumptions, an EF of $2 \times 10^5$ was calculated for the vibration mode at 1348 $cm^{-1}$.

Although comparable sensitivities and EF values have been reported for colloidal Au and Ag, as well as roughened metal surfaces, the use of our nanowire monolayers as SERS substrates has several advantages. First, the surface properties of these nanowire monolayers are highly reproducible and well-defined as compared to other systems. Second, the unique features of the nanowires, such as sharp vertices, non-circular pentagonal cross-sections, inter-wire coupling, may lead to larger field enhancement factors, offering higher sensitivity under optimal conditions. In addition, strong wire coupling within the monolayers enables SERS experiments with a broad selection of excitation sources. Lastly, these monolayers can readily be used for molecular detection in either an air-borne or a solution environment. Hence, our nanowire-based sensing scheme could have significant implications in chemical and biological warfare detection, national and global security, as well as medical detection applications.

EXAMPLE 2

Ag Nanowire Synthesis

Silver nanowires were prepared via the solution-phase polyol process, where silver salt is reduced in the presence of a stabilizing polymer. A solution of poly(vinyl pyrrolidone) (0.36M, 5 mL, MW=55,000, Aldrich) was prepared using anhydrous ethylene glycol (Aldrich) as the solvent and subsequently heated to 160° C. A room temperature solution of silver nitrate (Alfa Aesar) dissolved in ethylene glycol (0.12M, 2.5 mL) was then added drop-wise into the hot PVP solution at a rate of approximately 0.125 mL/min. Heat and stirring were kept constant during this step. Upon initial addition of silver nitrate to the PVP, the solution immediately turned a bright yellow color, indicating the formation of silver seed particles. As the addition proceeded, the solution underwent a series of color changes: orange, red, bright green, brown, and finally opaque olive green. An opaque gray-green solution containing a white iridescent precipitate indicated the formation of silver wires.

Spherical silver nanoparticles are byproducts of this synthesis, but can be removed using size separation. After synthesis, the wire solution was cooled to room temperature and diluted in a 1:30 ratio with ethanol. The dilute wire solution was centrifuged (1.7 krpm, 20 minutes). The products were collected and redispersed in ethanol. This process was repeated approximately six more times. The final pellet was dispersed in 10 mL of ethanol. This procedure removed excess PVP and gave a homogenous wire solution in terms of both shape and size.

EXAMPLE 3

Ag Nanowire Surface Functionalization

For Langmuir-Blodgett experiments, the surface of the nanowires must be hydrophobic. We functionalized our silver nanowires using long-chain alkanethiols, which readily adsorb onto the nanowire surface and displace PVP. A 100 µM solution of 1-hexadecanethiol in chloroform was added to the wire solution in a 1:1 ratio and then sonicated for approximately 5 minutes. After at least 10 hours, the solution was then transferred into glass vials and centrifuged (3.3 krpm, 15 minutes). The precipitates were collected and redispersed in chloroform. The hydrophobic silver wires readily precipitate out of chloroform as a beige solid. This process was repeated approximately six times to remove any excess thiol. The final solution appeared opaque gray or tan.

EXAMPLE 4

Ag Nanowire Langmuir-Blodgett Assembly

The solution of dispersed nanowires was spread drop-wise (typically 2.5 ml of $10^{10}$ wires/ml) onto the water surface of a Langmuir-Blodgett trough (Nima Technology, M611). The nanowires form a grayish layer on the water surface, which is compressed by a barrier with a speed of 30 $cm^2$/min (the width of the trough is 10 cm). The surface pressure was monitored with a Wilhelmy plate during the compression. The film was compressed to different surface pressures, and then deposited to various substrates, such as silicon and glass, for further studies. Typically, the substrates were dipped and then pulled vertically through the film with a speed of 2 mm/min.

EXAMPLE 5

Structural and Optical Analysis

The Ag nanowire monolayers were examined with an optical microscope equipped with cross-polarizers. The ordering of the nanowires within the monolayers was examined in detail using scanning electron microscope (JEOL 6430) and transmission electron microscope (Philip CM 200). The absorption spectra of the nanowire colloidal solution as well as the nanowire monolayers on substrates were collected using a HP 8453 UV-VIS spectrometer and an Acton UV-VIS/reflectance spectrometer, both equipped with a polarizer accessory. The resultant images under the cross polarizer are shown in FIG. 10A-B. The imaging area corresponds to 735 by 521 µm.

EXAMPLE 6

SERS Experiments on Nanowire Monolayer

Surface Raman spectra from the organothiol monolayers on Ag were recorded within 24 hours after preparation to minimize any effect of oxidation in air. Rhodamine 6G (Aldrich) was used as purchased. Starting with a R6G stock solution of $10^{-4}$ M, concentrations down to $10^{-10}$ M were prepared by successive dilution by factors of 10 or 100. After a 10-minute incubation in the corresponding R6G or DNT solution, SERS measurements were made in dry, ambient conditions.

The visible Raman spectra were recorded using a Holo-probe spectrometer (Kaiser Optical) equipped with a Nd:YAG laser frequency-doubled to 532 nm. The laser was operated at 25 mW with a spot size approximately 100 µm in diameter. To reduce photodecomposition, samples were rotated at 600 rpm. The Raman-scattered light was collected in the 180° direction (perpendicular to the substrate) and detected with an electrically-cooled CCD camera (256×1022 pixels) after cutting off the laser light with a high-performance holographic notch filter. The spectral resolution of the instrument is 5 cm$^{-1}$. The near-infrared Raman spectra were recorded using a Renishaw Raman spectrometer with 785 nm diode laser light. It was operated at 2 mW with spot size of 1-2 µm.

To summarize, Langmuir-Blodgett technique was used to assemble monolayers (with area over 20 cm$^2$) of aligned silver nanowires that are ~50 nm in diameter and 2-3 micrometers in length. These nanowires possess pentagonal cross-sections and pyramidal tips. They are close-packed, and are aligned parallel to each other. The resulting nanowire monolayers serve as excellent substrates for surface-enhanced Raman spectroscopy (SERS) with large electromagnetic field enhancement factors ($2 \times 10^5$ for thiol and 2,4-dinitrotoluene, and $2 \times 10^9$ for Rhodamine 6G) and can readily be used in ultrasensitive, molecular-specific sensing utilizing vibrational signatures.

EXAMPLE 7

2-Dimensional Tiling with Shaped Nanocrystals

We synthesized gold nanorods with controlled aspect ratios by using photochemistry in the presence of silver ions. The process was a simple photo-reduction of gold ions in the presence of silver ions. It was observed that the color of the resulted solution varied with the amount of silver ions added, which is indicative of gold nanorods with different aspect ratios. FIG. 11 shows the UV-VIS spectra for various solutions prepared with different amounts of silver ion addition. Curve A in FIG. 11 shows the spectra when no silver ion solution was added and consisted of mostly spherical particles. The UV-VIS spectrum exhibits single absorption peak at 530 nm. Curves B through E in FIG. 11 show the spectra as increasing amounts of silver ion solution (silver nitrate) are added. When silver ions were added, gold nanorods formed which can be seen from the additional absorption peak due to the longitudinal surface plasmon in the UV-VIS spectrum. Typically their UV-VIS spectra show one transversal surface plasma peak at 520 nm and longitudinal ones at 600-800 nm.

FIGS. 12A-C show transmission electron microscopy (TEM) images of gold nanorods produced by addition of increasing amount of silver nitrate solution. The average aspect ratios for these rods can be increased from one to ten. FIG. 13 shows a high-resolution TEM image of one of the nanorods. The crystallographic facets are the same as the electrochemically synthesized gold nanorods, with the growth direction being [001] and the side mostly covered with {001} and {110} facets. When the aspect ratio is 1, virtually nano-cubes of Au were obtained.

The exact mechanism how these foreign ions effects the particle growth habits can be examined through systematical time-resolved UV-VIS absorption and transmission electron microscopy studies. A natural question is whether it is possible to use other metal ions or use different ionic strength to affect the final crystal habits. However, by adding different organic molecules/polymers, we have arrived at some interesting synthetic conditions for obtaining crystals of different shapes. Such shapes can be determined empirically through experimentation. Other factors that may affect shape are concentrations, temperature, different surfactants and cosurfactants, foreign ion addition, and ionic strength. These nanocrystals, with their uniform sizes and shapes, are ideal building blocks for Langmuir-Blodgett monolayer formation. Additionally, purity and yield are important.

As described above, the Langmuir-Blodgett (LB) technique is a very powerful assembly approach with several appealing characteristics. First, a large area of ordered nanocrystal monolayer is formed which can be easily transferred onto other substrates, and it is also fairly easy to carry out multiple or alternating layer deposition. In addition, the interparticle distance and the final superstructures can be finely tuned via control of the compression process. Fundamentally, this would be an interesting issue of 2-dimensional tiling with uniform nanoscale "tiles".

For Langmuir-Blodgett films of various nanoparticles such as Ag, Au, and CdS where the nanoparticles are spherical, the particles form a gas phase at low densities, and the monolayer is highly compressible without significant increase in the surface pressure. Depending on the particle size, the length of the capping ligand, and the surface pressure, various microscopic structure of islands, wires, and rings composed of the nanoparticles can be formed. As the monolayer is compressed, the particles start to form a condensed phase, usually a hexagonally close packed structure due to the isotropic inter-particle interactions.

In contrast to spherical nanoclusters, several fundamental questions immediately arise in order to form well-defined 2D or 3D assemblies of the shaped nanocrystals such as (1) how will the shape, aspect ratio and size of the nanocrystals affect their organization behavior, (2) will their assembly behavior fundamentally differ from the mesoscale assembly that has been extensively studied by the Whiteside's group at Harvard, (3) what kind of ordered (super) structures can be expected, and (4) how will the collective properties correlate with the structures of these assemblies?

As described above, we have applied the Langmuir-Blodgett technique to the assembly of one-dimensional nanostructures such as nanorods and nanowires. The methodology we used for nanorod assembly exemplifies the approach that we will adopt for nanocrystals of other shapes. First, these 1D nanostructures are rendered hydrophobic by surfactant surface functionalization. It was found that the surface pressure π of the nanorod monolayer follows a π-A (area) curve that is commonly observed during the LB compression of amphiphilic surfactants or surfactant capped nanoclusters on the water surface. Superstructure formation from these anisotropic nanoparticles, however, displays much more complex behavior than the spherical particles, as we have observed with $BaCrO_4$, $BaWO_4$, and Au nanorods. We have also observed that superstructure formation is highly dependent on the aspect ratio of the nanorods and the collective interactions among these individual units.

FIG. 14A-D are transmission electron microscopy images of nanorod assemblies at water/air interface at different stages of the compression, where FIG. 14A shows isotropic distribution at low pressure, FIG. 14B is monolayer with nematic arrangement, FIG. 14C is a monolayer with smectic arrangement, and FIG. 14D is a nanorod multilayer with nematic configuration, and where the insets in FIG. 14B and FIG. 14D are the Fourier transform of the corresponding image. For nanorods with short aspect ratio (~3-5) such as the $BaCrO_4$ nanorods (diameters, ~5 nm), they form raft-like aggregates of generally three to five rods by aligning side-by-side due to the directional capillary force and the van der Waals attraction at low densities (i.e. low surface pressure). These aggregates are dispersed on the subphase surface in a mostly isotropic state (FIG. 14A). As the monolayer is compressed, the nanorods start to align into a certain direction and form a nematic phase (FIG. 14B). With further compression, nanorod assemblies with smectic arrangement are obtained (FIG. 14C), which is characterized by layer-by-layer stacking of ribbon-like nanorod superstructures. During this compression, the areal density of the nanorods also increases significantly from ~500 to ~5000/μm². Above certain pressure, the monolayer breaks into multilayers, where it resumes a disordered 3-dimensional (3D) nematic configuration (FIG. 14D). The overall nematic arrangement in the multilayer nanorod superstructures is frequently disrupted by singularities such as disclinations.

This LB technique was also applied to the thiol capped Au nanorods (diameter ~8 nm) of similar aspect ratio. However, it is observed that these metal nanorods have great tendency to form nanorod ribbons spontaneously. In these nanoribbon superstructures, many Au nanorods align side by side. Compression of these nanorod monolayers does not exhibit the same phase evolution as seen in the $BaCrO_4$ system. In most cases, isotropic arrangements of the Au nanorod ribbon structures are "quenched" during the compression. This difference can be attributed to the much greater attractive van der Waals and directional capillary interaction among Au nanorods as compared with the $BaCrO_4$ nanorods as well as the polydispersity of the available Au nanorods.

On the other hand, the organization of the $BaWO_4$ nanorods (diameter ~10 nm) with large aspect ratio (~150) again differs significantly from the assembly of the short $BaCrO_4$, Au, and CdSe nanorods where ribbon-like and vertical rectangular/hexagonal superstructures are often favored. With low surface pressure, these nanorods are fairly dispersed; the directors of nanorod are isotropically distributed, and no superstructures can be observed. After compression, these nanorods readily align in a roughly same direction and form a nematic layer. With strong compression, these nanorods form bundles that have almost perfect side-by-side alignment between nanorods. The preference of nematic phase formation upon compression is a distinct character of the assembly behavior for nanorods of large aspect ratio, Our experiments on nanorod assembly using the Langmuir-Blodgett technique clearly indicates that the formation of a superstructure is a highly complex phenomena and is largely determined by the interactions between the nanocrystals and their aspect ratio/shape. Both entropy and energy considerations are important here in order to account for the complex self-organization behaviors of these highly anisotropic nanoparticles. In a solution of rigid nanorods with sufficient monodispersity, a competition between two types of entropy exists: for low concentrations of nanorods the orientational entropy dominates and will be maximized by an isotropic distribution, whereas for high concentrations the packing entropy becomes more important which will favor more ordered structures. Possible ordered structures include orientational and positional ordered hexagonal mesophase and orientational ordered nematic, smectic liquid crystal, lamellar and columnar structures. This ordering occurs in order to maximize the entropy of the self-assembled structure by minimizing the excluded volume per particle in the array. Additional interparticle forces can be classified into two main categories: repulsive and attractive. More specifically, for charged colloidal particles, the most commonly used effective pair potential consists of a van der Waals attraction and a screened Coulomb repulsion term. In addition, this interaction contains other components of electrostatic repulsion, van der Waals, solvation, and steric surface forces. Both hard inter-object interactions (entropy term) and soft molecular interactions (energy term) will contribute to determine which superstructure ultimately the nanorods will form.

The assembly behavior of realistic nanorods would deviate from those of ideal hard rods due to the existence of significant van der Waals interaction and directional capillary interaction. Strictly, none of our experimental 1D nanostructures can be considered as ideal hard rods. For example, in explaining the tendency of nanorods to align parallel to each other, another reason would be the higher lateral capillary forces along the length of a nanorod as compared to its width. This anisotropy of interaction between nanorods could be one important driving force for the side by side alignment of nanorods rather than end to end. It is also true that between any two bodies of matter there is an attractive van der Waals force caused by the interaction between the fluctuating electromagnetic fields associated with their polarizabilities. The attraction between two atoms separated by distance r goes as $r^{-6}$ (the Lennard-Jones potential) and the interaction between two spherical particles of radius R, obtained by summing over all pairs of atoms, is $$V_A(r) = -\frac{A}{6}\left[\frac{2R^2}{r^2-4R^2} + \frac{2R^2}{r^2} + \ln\left(1 - \frac{4R^2}{r^2}\right)\right]$$

where r is now the center-to-center separation. The strong directional capillary and van der Waals interaction between the Au nanorods explains well why their 2-dimensional assembly process deviates significantly from the ideal hard rod system.

While the existence of strong attractive interactions among the nanorods would complicate their assembly process, it should be recognized that these interactions could also be systematically tuned in order to form desired nanorod superstructures. For example, the Hamaker constant A in the van der Waals attraction term is determined by the material properties of the particles and suspension medium, in particular their frequency-dependent polarizabilities. Of relevance here is the fact that if the particles and liquid have equal polarizabilities, then A=0. Thus if the refractive indices of the particles and liquid are matched, van der Waals attractions are expected to be negligible. Consequently, the interaction between the nanorods can be modified as desired. The surface functionality of the these 1D nanostructures plays significant roles in regulating the attractive and repulsive interactions among these individual units, consequently determining their final 2-dimensional or 3-dimensional superstructures. Aligning these 1D nanoscale building blocks into nematic or smectic phases has its significance in both fundamental study of the structure-properties correlation of nanostructures and the technological important areas such as formation of high density logic and memory devices.

Figure 15A:
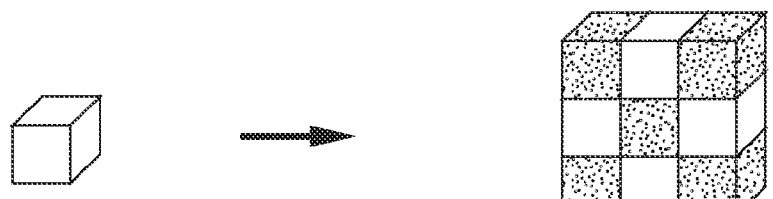
Figure 15B:
Figure 15C:
Figure 15D:
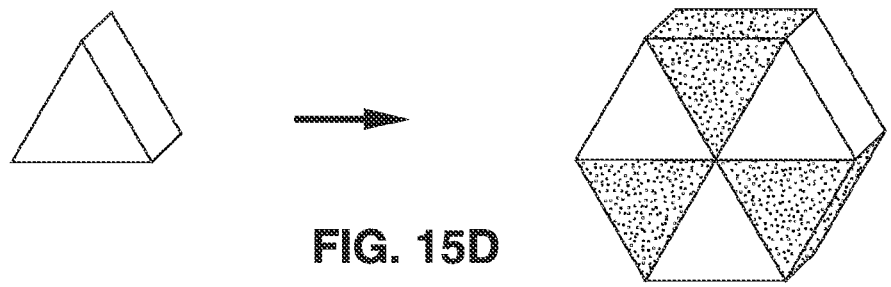
Figure 15E:
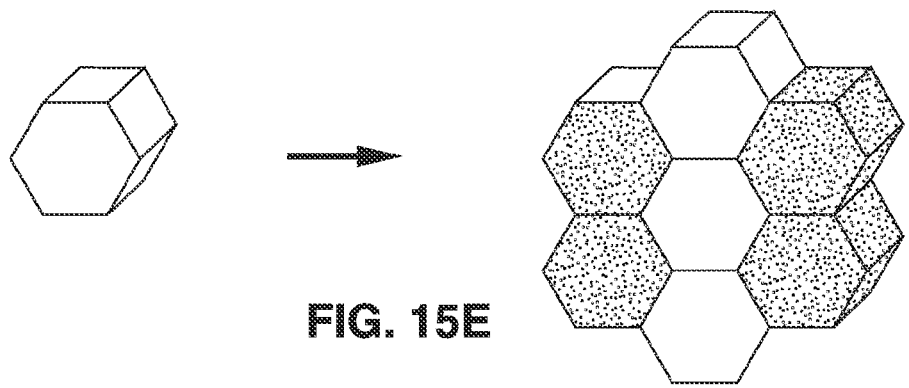

With this nanorod assembly in mind, the Langmuir-Blodgett technique can be adapted for 2-dimensional assembly of other shaped nanocrystals. For such other shaped nanocrystals, the nanocrystal colloidal suspension is spread dropwise on the water surface of a Langmuir-Blodgett trough. The nanocrystal surface layer is then compressed slowly. At different stages of compression, the nanocrystal assemblies at the water-air interface are then transferred carefully onto TEM grids covered with continuous carbon thin film using the Langmuir-Schäffer horizontal liftoff procedure. The superstructures of the assemblies are then examined systematically using TEM. The phase diagram for the assembly of nanocrystals of different shapes is then explored in a similar fashion (i.e., surface functionalization and Langmuir-Blodgett assembly. FIG. 15A-E are schematic diagrams showing the organization of shaped nanocrystals according to an embodiment of the invention, with FIG. 15E representing a possible superstructure.

Once empirical data is collected for the single component assembly, the experiments will be extended to the study of bi-component assembly at 2-dimension (i.e., monolayer assembly of mixture of uniform dots and rods or others). In this study, interaction between these two components will be modified through surface functionalization and their assembly behavior will be examined in a similar fashion as we have carried out for the single component system.

Finally, the monolayer of the ordered nanocrystals will be embedded in an inorganic (e.g. $SiO_2$) or polymer matrix in order to obtain continuous form of the monolayer that can be manipulated in a macroscopic form. This can be accomplished by polymerizing and cross-linking the monolayer on the water surface after the assembly process. These monolayer metal nanocrystal/matrix composites are expected to be flexible, easy to manipulate and can be readily applied in catalytic and sensing application.

EXAMPLE 8

Platonic Gold Nanocrystals

Known to the ancient Greeks, there are five Platonic solids that can be constructed by selecting a regular convex polygon and having the same number of them meet at each corner: tetrahedron, octahedron, hexahedron (cube), icosahedron, and dodecahedron. The beauty in their symmetry and their apparent simplicity continue to inspire generations of mathematicians and scientists. In nature, certain viruses and radiolaria also routinely take the form of these polyhedral shapes. Recently, the concept of shape control has started to revitalize the centuries-old metal colloidal synthesis. Nanoparticles of various shapes (e.g., rods, wires, prisms, cubes), particularly those of silver and platinum, have been prepared using a variety of different methodologies. The preparation of nanoparticles of highly symmetric Platonic shapes with a unified method, however, has yet to be demonstrated, and is by itself a scientific curiosity and great challenge that requires exquisite crystal growth control.

Herein, we describe a systematic shape-evolution of gold nanocrystals with sizes of 100-300 nm in a modified polyol process. By adding surface-regulating polymer and foreign ions, we can readily access the distinct shapes of tetrahedron, cube, octahedron, and icosahedron (dubbed Platonic Nanocrystals) with high yield and good uniformity. These nanocrystals have the perfect symmetry for 2- and 3-dimensional packing and therefore could enable the rational tuning of their optical, electrical, and catalytic properties.

Gold nanocrystals were produced via a modified polyol process, with the presence of the surface-regulating polymer poly(vinyl pyrrolidone) (PVP). Briefly, ethylene glycol solutions of hydrogen tetrachloroaurate ($HAuCl_4 \cdot 3H_2O$) and PVP were injected simultaneously into boiling ethylene glycol. Ethylene glycol served both as the solvent and reducing agent for the reaction. PVP not only stabilized the particles but also controlled the shape of the particles. The molar ratio between the PVP and the gold precursor was kept between 4.3 and 8.6. Gold particles formed within minutes, and the color of the final diluted colloidal solution was iridescently blue.

Transmission electron microscopy (TEM) imaging showed that the majority (~70%) of the particles had a triangular shape (FIG. 16A), and sizes of 210±20 nm. Electron diffraction of a single particle (FIG. 16B, inset) showed that the particle was single crystalline, with the top and bottom covered with {111} surfaces. This initial inspection of the TEM data suggests the formation of flat nano-prisms as have been reported previously for silver. Detailed scanning electron microscopy (SEM) studies, however, revealed otherwise. FIG. 16A-E are images of shaped nanostructures according to the present invention, wherein FIGS. 16A and B are TEM images of truncated tetrahedral gold nanoparticles and the inset in FIG. 16B is the electron diffraction pattern taken along the [111] zone axis from the particle shown in FIG. 16B, and FIGS. 16C and D are SEM images of several partially developed gold tetrahedra. Interestingly, the sides of the particles were clearly slanted (FIG. 16C, D). This indicates that rather than being flat prisms, these particles can be more accurately described as tetrahedra with a truncated corner, or as partially developed tetrahedra (hereafter we will call them tetrahedra for simplicity). The surfaces of these particles are dominated with {111} planes, which make them energetically favorable compared to prisms with other high-energy side surfaces such as (1 $\bar{1}$ 0) or (11 $\bar{2}$). Occasionally, we were able to observe similar-sized particles with nearly fully-developed tetrahedral shapes (FIG. 16D), which points to the possibility of obtaining gold tetrahedra upon further growth of these triangular particles.

Figure 18:
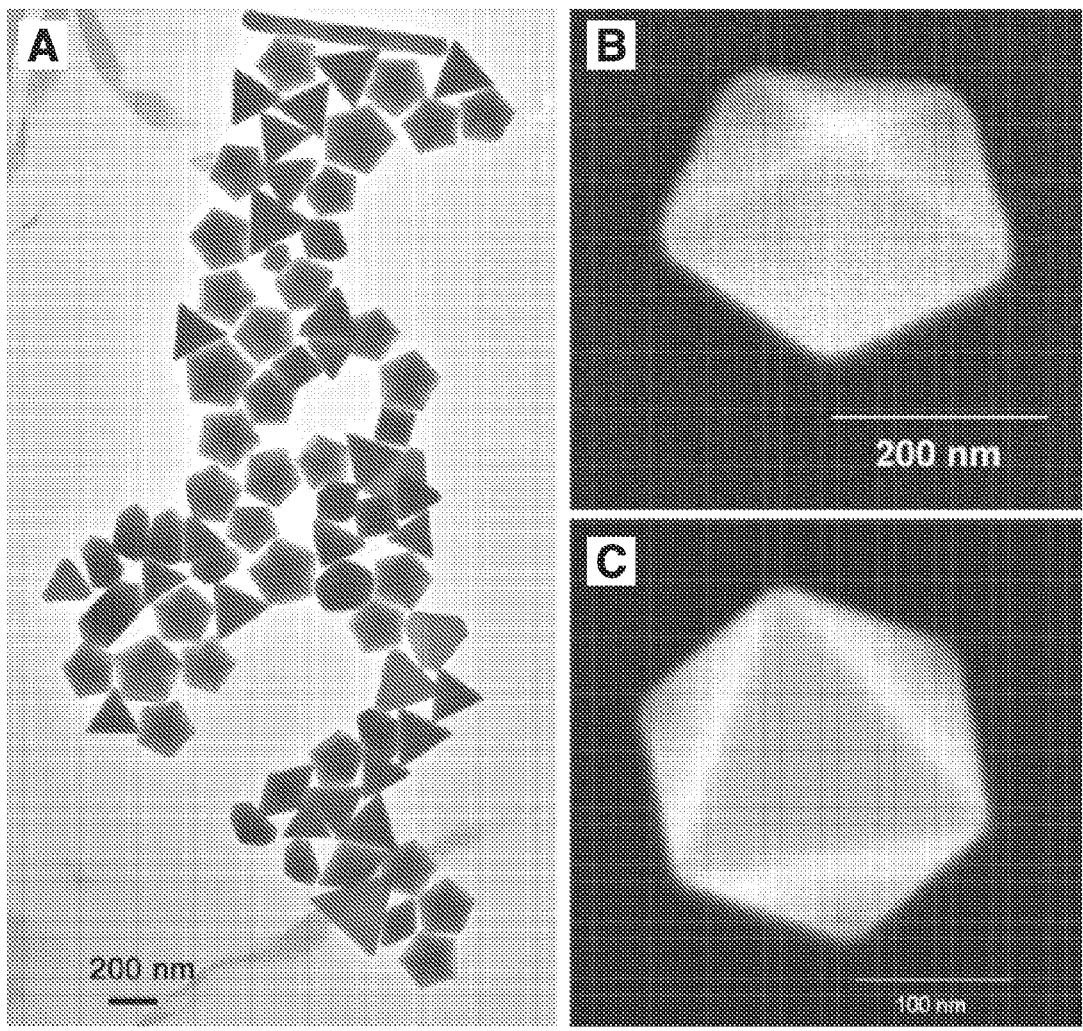

It was found that the nanoparticle shapes were highly sensitive to the gold precursor concentration used in the experiments. By slightly reducing the gold precursor concentration, we were able to produce nanocrystals with icosahedral shapes. In one particular example, the gold precursor concentration was reduced to ⅘ of that used for the synthesis of tetrahedra, and the final molar ratio between the PVP and the gold precursor was maintained at 8.6. FIG. 17A-B are images of icosahedral nanocrystals according to the present invention wherein FIG. 18A is a TEM image and FIG. 17B is a SEM image of icosahedral gold nanoparticles, and wherein the inset in FIG. 17B shows clearly all {111} facets of a typical icosahedron. Observation by TEM showed that >90% of the particles had a projected hexagonal shape (FIG. 17A) and sizes of 230±20 nm. The size of a particle is defined here as the distance from one edge of the hexagonal projection to the opposite side. Electron diffraction on a single particle showed a complex pattern, indicating that the particle was composed of multiple crystal domains. Further investigation with SEM showed that the particles were mostly icosahedra (FIG. 17B and inset). Note that icosahedral particles of fcc metals represent one of the most investigated multiply twinned particles (MTP) in gas phase experiments. Our observation, however, is the first time that uniform metal particles with such complex yet well defined structures and sizes ranging from several tens to hundreds of nanometers have been prepared in solution. In addition to the shapes of tetrahedron or icosahedron, which formed the majority of the product, a small portion (~10%) of decahedra (another type of MTP) and regular octahedra were also commonly observed in the final products as can be seen from FIG. 18 which shows TEM and SEM images of some minority particles observed during synthesis according to the present invention wherein FIGS. 18A and B shown decahedrons and FIG. 18C shows an octahedron.

Tetrahedra and icosahedra represent two of the Platonic solid shapes that are covered with the {111} family of planes. Further shape control can be achieved by introducing foreign ions during the nanocrystal growth process. For example, addition of small amount of silver ions prior to the gold tetrahedron synthesis yields uniform gold nanocubes. Typically, 0.5 ml of a 0.0059 M silver nitrate ($AgNO_3$) solution (1.1% of the gold precursor) in ethylene glycol solution was injected into the boiling ethylene glycol five minutes before the injection of the gold precursor and the PVP. The color of the final colloidal solution was iridescently bluish-purple. TEM and SEM observation showed that gold nanocubes (>95%) of average size of 150±14 nm were produced. FIG. 19A-D are TEM and SEM images of gold nanocubes according to the present invention dispersed on a TEM grid and a silicon substrate wherein the inset in FIG. 19C shows the electron diffraction pattern recorded along the [100] zone axis of a gold nanocube shown in FIG. 19D. Electron diffraction (FIG. 19C inset) on a single particle showed that the cube is a single domain, with {100} surfaces.

While SEM and TEM often sample only a small portion of the products, X-ray diffraction (XRD) can be used to assess the overall quality and purity of these facetted nanoparticles. Three XRD patterns recorded on three different shapes are compiled in FIG. 20. All peaks can be readily assigned to the (111), (200) and (220) planes of fcc gold. Comparison of the (111) and the (200) diffraction intensities reveals very interesting features that are intrinsically related to the shapes of the particles being examined. For the gold nanocube sample, the intensity ratio between the (200) and the (111) diffractions is 1.93, which is significantly larger than the conventional bulk intensity ratio (~0.53). This is a clear indication that the faces of these nanocubes, primarily composed of {100} planes, tend to preferentially orient parallel to the supporting substrates, giving significantly high (200) diffraction intensity. On the other hand, the intensity ratios between the (200) and the (111) diffractions are much smaller than the bulk values for the tetrahedron and icosahedron samples, being 0.25 and 0.31, respectively. This again indicates that for tetrahedron and icosahedron samples, the {111} family of planes is dominant. This set of XRD patterns unambiguously demonstrates our capability of synthesizing with a high degree of selectivity, gold nanoparticles of different Platonic shapes.

The optical properties of metal nanoparticles are highly dependent on the size and shape of the particles. This has been extensively explored both theoretically and experimentally on several systems including gold nanorods, silver nanorods, prisms, and cubes. Several groups have theoretically simulated the optical properties of metal nanoparticles with arbitrary shapes and found distinctive shape-dependent behaviors. UV-VIS spectra collected on the ethylene glycol (EG) solutions of these three different shapes are compiled in FIG. 21. It was found that gold nanoparticles of different shapes clearly displayed different surface plasmon resonance, 621 nm for the nanocubes, 626, 950 nm for the tetrahedra and 613, 950 nm for icosahedra. The spectral features of the nanocube and tetrahedron are fairly consistent with previous theoretical simulations. The UV-VIS spectrum of the icosahedron nanoparticles resembles that of spherical nanoparticles of similar size. The additional broad, near IR peak, is most likely the result of co-existing triangular particles.

It is commonly accepted that the shape of an fcc nanocrystal is mainly determined by the ratio (R) between the growth rate along <100> and <111> direction. Tetrahedra and icosahedra bounded by the most stable {111} planes will be formed when R is large (~1.73), and perfect cubes bounded by the less stable {100} planes will result if R is reduced (~0.58). The surface regulating polymer (PVP) and the introduction of foreign ions are believed to play the key roles here. Selective interaction between PVP and the different surface planes of the gold nanocrystals could greatly enhance the growth rate along the <100> direction, reduce the growth rate along <111> direction, and ultimately result in particles with tetrahedral or icosahedral shapes. The mechanism for the selective growth of icosahedral nanoparticles vs. tetrahedral ones is yet to be determined. The fact that lower overall gold precursor concentration (with otherwise identical synthetic conditions) results in selective icosahedron growth suggests that subtle differences in the gold embryonic seed formation and their subsequent growth might lead to this shape selection.

Offering another means of shape control, the introduction of foreign ions could greatly influence the relative growth rates along certain directions. We believe that the introduction of silver ions in the current process can significantly reduce the growth rate along the <100> direction and/or enhance the growth rate along the <111> direction, and ultimately particles with cube shapes result. There have been previous studies where the introduction of silver impurity during gold particle formation resulted in the control of the nanocrystal shape. For example, silver ions were used to control the aspect ratio of the gold nanorods produced via electrochemistry and photochemistry. It is also interesting to note that our shape control scheme is vastly different from what has been reported by other researchers in the silver system, where PVP interaction promotes the nanocube formation. This could be the result of different interfacial interaction with polymer between the gold and silver systems.

The successful preparation of gold Platonic nanocrystals exemplifies the exquisite shape control that can be achieved through careful growth rate regulation along different crystallographic directions, and demonstrates a strategy that could be generally applicable to other material systems. These Platonic nanocrystals have perfect symmetry for 2- and 3-dimensional packing, and therefore, could lead to interesting research on nano-tectonics, the formation of high-order nano-/microstructures, and finally, the rational tuning of optical, electrical, and catalytic properties.

For a typical tetrahedron synthesis, 5 ml of ethylene glycol (EG) was boiled in a silicone oil bath at 280° C. under reflux while stirring with a magnetic bar. Nitrogen was continuously flowed through the entire refluxing system. Solutions of 0.375 M PVP in EG, and 0.083 M HAuCl$_4$.3H$_2$O in EG were prepared. The PVP solution was injected to 5 ml of boiling EG, using a micropipette, and then the HAuCl$_4$ solution was injected twice. This process was repeated 15 more times for every 30 seconds. The solution turned red within 8 minutes after the injection, indicating formation of gold nanoparticles. The solution was aged for 45 minutes to ensure that the reaction was complete. The solution was collected, and the large aggregates and unreacted salts were removed by centrifugation. The solution was centrifuged at 1,000 rpm for 5 minutes and the precipitate was removed. After repeating this 3 times, the solution was centrifuged at 3,500 rpm for 30 minutes. The precipitate was collected and redispersed in 4 ml of EG.

For the synthesis of icosahedra, the gold precursor concentration was reduced to ⅘ of that used in the synthesis of tetrahedra under otherwise similar conditions.

For the synthesis of nanocubes, 0.5 ml of 0.0059 M silver nitrate (AgNO$_3$) solution in EG was first added to the boiling EG 5 minutes before the injection of gold precursor and PVP.

Typically, for the icosahedral and tetrahedral particle syntheses, the solution turns from light pink-orange to strong rust-red 7 minutes after the injection is finished. When diluted, the solution becomes iridescently blue. For the cube synthesis, the reaction solution shows a similar color change around 4 minutes after the injection is finished.

EXAMPLE 9

Ag-Assisted Shape Control of Pt Nanocrystals

Metal nanocrystals with precisely controlled shape exhibit unique optical, magnetic, and catalytic properties. There have been extensive studies on approaches to control size and shape of the metal nanoparticles, and most of the methods developed thus far can be categorized as either reduction or decomposition of the metal precursors in the presence of organic capping reagents in solution. Cetyltrimethyl ammonium bromide (CTAB) and poly(vinylpyrrolidone) (PVP) have been widely used as regulating agents for the selective growth of nanocrystals with well-defined shapes such as rods, prisms, and cubes. However, exact binding nature between these capping reagents and the specific crystallographic planes is still ambiguous, and there are no generalized mechanisms interpreting various metal nanocrystal shape control experiments.

Many researchers have tried to make different shapes of the Pt particles in order to investigate their influence on catalytic activity. Herein we report the synthesis of monodisperse Pt nanocrystals with various shapes such as cubes, cuboctahedra, and octahedra selectively in high yields. We found that silver ion (or AgCl) enhances the crystal growth rate along <100>, and essentially determines the shape and surface structure of the Pt nanocrystals. This process may be applicable for other metal and semiconductor nanostructures, and may provide insights for a general mechanism on morphology control of nanocrystals.

In a typical synthesis, 0.5 mL of AgNO$_3$ solution in ethylene glycol (EG) was added to the boiling EG. EG solutions of PVP (93.8 μL of 0.375 M) and dihydrogen hexachloroplatinate (H$_2$PtCl$_6$.6H$_2$O, 46.9 μL of 0.0625 M) were added to the mixture every 30 sec over 16 min. The color of the solution immediately changed to dark brown indicating the fast reduction of Pt(IV) to Pt(0) species. The solution was refluxed for additional 5 min. Without adding Ag ions, the particles were obtained as a mixture of different shapes. However, when 1.1 mol % of AgNO$_3$ (with respect to the Pt concentration) was introduced to the solution, Pt cubes (~80%) were dominant products with a small amount of tetrahedra (~10%). Transmission electron microscopy (TEM) image (FIG. 22A) shows that the Pt cubes are homogeneous in shape with a narrow size distribution (face-to-face: 7.12±0.58 nm, vertex-to-vertex: 9.37±0.61 nm). High resolution TEM (HRTEM) image (FIG. 22B) demonstrates the exposed {100} surface of the cube oriented along the [001] zone axis. Distance between the adjacent lattice fringes is 1.96 Å, in good agreement with the interplanar distance of the (200) plain in the face-centered cubic (fcc) Pt structure. FIG. 22C shows a triangular projection of the minor tetrahedral particles along the [111] direction, in which all side faces are covered with {111} planes.

Increasing the AgNO$_3$ concentration to 11 mol % changes the morphology of the Pt particles. Mostly faceted particles were obtained, including hexagons as the majority (FIG. 23A). The Pt nanocrystals are monodisperse with the largest vertex-to-vertex distance of 9.06±0.62 nm. FIG. 23B is a representative HRTEM image of the hexagon, and clearly shows the lattice fringe image of {111} planes with the interplanar distance of 2.26 Å and the separation angle of 70°, consistent with the hexagonal projection of ideal cuboctahedron along the [110] zone axis (FIG. 23C). In this projection, four {111} and two {100} facets are placed on the edges of the hexagonal shape.

At higher concentration of AgNO$_3$ up to 32 mol %, the resulting Pt nanocrystals are dominated by diamond and square shaped particles (~65%) as well as tetrahedra (~17%) (FIG. 24A). The average vertex-to-vertex distance of the major particles is 9.78±0.63 nm. FIG. 24B shows HRTEM image of a diamond shaped particle, which turns out to be the [110] oriented Pt octahedron. The square projections are not from the Pt cubes, but from the same octahedra oriented along the [001] zone axis. FIG. 24C exhibits four {111} facets edged on the Pt octahedron, while four {100} planes are located on the edges of the Pt cube along the same direction.

It is commonly believed that the final morphology of the fcc nanocrystals is dependent upon the R value, defined as the relative growth rate along the <100> direction to that of the <111>. As the concentration of Ag ion increases in the reaction mixture, the majority of the Pt particles changes from the cubes (R=0.58) to the cuboctahedra (R=0.87), and eventually to the octahedra (R=1.73). It reveals that introduction of Ag ion enhances the growth along <100>, and/or suppresses the growth along <111>. Controlled experiments were carried out to support this reaction mechanism. It was found that Ag ions were reduced into Ag clusters at EG reflux without PtCl$_6^{2-}$. In the presence of Cl$^-$, white AgCl colloids were immediately formed, but also reduced into Ag clusters under the same condition. The reduced silver clusters/species seem to be preferentially adsorbed on more active {100} surfaces of the Pt nuclei than {111} facets during the reaction. Note that the desorption energy of Ag on Pt(100) single crystalline surface is higher than that on Pt(111) in the Ag monolayer film growth, indicating the relative stability of Ag(0) on the Pt{100} surface. When the Pt precursors were continuously added, the Pt salts were reduced spontaneously with oxidation of the adsorbed Ag species on the {100} surface by favorable electrochemical reaction (4Ag+H$_2$PtCl$_6$→4AgCl+ Pt(0)+2HCl), and subsequently the growth rate along the <100> direction was enhanced with the dissolution of AgCl into solvent. As a result, silver atoms will not be incorporated into the nanocrystal lattice. Actually, there are no detectable silver signals in all the Pt nanocrystals in this study checked either by X-ray diffraction (XRD) or energy dispersive X-ray spectroscopy (EDS) after simple purification.

Other conditions such as reaction temperature and addition rate of the reactants are also important to make uniform Pt nanocrystals. For instance, smaller Pt particles were generated with the size of 3.73±0.39 nm at 160° C. under otherwise same reaction condition. On the other hand, slow addition of the PVP and Pt salt solutions over 30 min led to polycrystalline particles larger than 13 nm.

It is interesting to point out that previously reported gold nanorod synthesis by photochemical and electrochemical methods may follow this analogous mechanism. Introducing Ag ions enhances the <100> directional growth, and subsequently controls the aspect ratio of the nanorods. We believe that this process can be expanded to other metal and semiconductor systems using various foreign ions as shape control agents.

Nanoparticles of different shape exhibit intrinsically different surface structures. Considering the ideal models, the cube has only {100} faces, and the octahedron and tetrahedron display only {111} surfaces. In the cuboctahedron, the surface is composed of six {100} and eight {111} planes with a relative area of 1:0.577. Accordingly, surface dependent properties such as catalytic reactivity can be modified rationally by manipulating the shape of the particles with a variation of added silver ions.

FIG. 25 is a generalization of the modified polyol process described above.

In conclusion, monodisperse Pt nanocrystals with various shapes including cubes, cuboctahedra, and octahedra have been synthesized selectively by a modified polyol process. The addition of silver ion was found to enhance the crystal growth rate along <100>, and essentially determines the shape and surface structure of the Pt nanocrystals. This process may be applicable to other metal and semiconductor systems using various foreign ions as shape control agents. We also expect that the surface dependent properties such as catalytic reactivity can be regulated rationally by manipulating the shape of these particles. Therefore, the Ag ion plays an important role to control the shape and surface structure of the Pt nanocrystals.

EXAMPLE 10

Nanocrystal Lithography Using Langmuir-Blodgett Technique

The integration density of microelectronic devices on a silicon-based chip exhibits phenomenal rate of increase by rapid development of optical lithography. Recent progress of lithographic techniques can commercialize the microprocessors with feature size of ~100 nm in a high yield. However, these "top-down" approaches based on photolithography have a fundamental limit on the minimum length scale that can be ultimately attained, and increase the cost exponentially to obtain higher resolutions. Shorter wavelength light sources such as extreme ultraviolet and X-ray were introduced and regarded as strong candidates for achieving dimensions of several tens of nanometers. Although electron beam lithography is one of the most powerful tools for high-resolution capabilities less than 10 nm, it has critical problems of low throughput and slow processing speed. Alternatively, new techniques without using optical sources have been devised and applied for fabrication. Dip-pen lithography based on scanning probe microscopy can transfer various materials to the nanosized patterns, and nanoimprint technique provides a simple, low cost, and high-resolution fabrication down to ~10 nm. But no obvious successor to the current lithographic techniques has emerged yet.

On the other hand, nanoscale materials including quantum dots and nanowires are of massive interest in unique physical properties due to their low dimensionality. Considerable efforts have been focused on the synthesis and fabrication of the devices using individual nano-objects. If these nanoscale building blocks can be organized hierarchically into well-designed patterns, they will offer many important applications from nanoscale electronics and optoelectronics to molecular sensing. Microfluidic and electrical methods were partially successful to guide the low dimensional materials into the functional networks such as 3×4 crossed arrays. But there are crucial challenges of these "bottom-up" approaches such as the limit of scalability and extremely high error rate of assembly. Even if all problems can be completely resolved, the application for real industrial production may not be possible in the near future due to the high expense of changing entire process built on silicon microelectronics.

Advances in "top-down" lithography and "bottom-up" self-assembly techniques seem to merge with each other in terms of the nanoscale size range (10~100 nm). What if two opposite strategies combine synergistically in the same process? Simple synthetic schemes of the nanoscopic materials in a bottom-up approach can reduce rather sophisticated multistep deposition-etch processes in top-down lithographic techniques, and high reliability of top-down approach may be able to compensate repetitive production of the registered structures from bottom-up synthesis. Most of all, newly developed patterning skills can directly be employed to the current silicon-based manufacturing process. Two intriguing techniques have been reported thus far along this line. The self-assembled structures of block copolymer were transferred to the silicon nitride-coated substrate by reactive ion etching (block copolymer lithography). Close-packed layers of silica spheres have also been used as a mask for patterning metal nanoparticle arrays (nanosphere lithography). Both are inexpensive, simple, and high throughput techniques generating nanometer scale structures, but have limitations to make various shapes and arrays in the controlled positions by spontaneous self-assembly.

For developing more versatile self-assembled structures, we have suggested Langmuir-Blodgett (LB) technique for the assembly of low dimensional materials including nanoparticles, nanorods, and nanowires. Originally, the Langmuir-Blodgett technique has been developed for preparing mono- and multilayers of fatty acids and many other amphiphilic molecules that can be floated on the surface of water. It has been used extensively in the preparation of monolayers for molecular electronics, and more recently to create nanocrystal monolayers with tunable electronic and optical properties. Now it has been figured out that any materials in the nanoscale regime from a few to several hundreds of nanometer can be assembled to the close-packed monolayer by the same technique. The nanoscale materials were functionalized by hydrophobic ligands and dispersed onto a water surface of the Langmuir-Blodgett trough. Then the floating materials were compressed to high density on the surface by precise control of mobile barriers. This assembly process is a microscopic version of "logs-on-a-river". The compressed monolayer can be transferred onto any substrates such as silicon wafers or plastic substances.

There are several advantages of Langmuir-Blodgett assembly compared to the aforementioned techniques. First, any materials in a wide range of size can be deposited onto various substrates. There are huge amount of nanostructures from tiny nanoparticles less than 1 nm to nanowires up to □m scale in length. Second, the interspacing of nanoparticles and the pitch of nanowires can be rationally controlled through the compression process. This is important if the nanoscale materials are integrated into the high-density devices. Third, Langmuir-Blodgett assembly is a one-step and fast process, and technically has no limits of the area that can be obtained. The aligned area is limited only by the amount of initial materials used, and the sized of a trough area. Fourth, it is possible to transfer monolayers, layer by layer, to form parallel and crossed-nanowire structures for active device components.

Using the arrays of well-defined nanoscale materials by LB experiment, we have developed a new lithographic technique which we refer to as "nanocrystal lithography"; that is, nanocrystal arrays as direct patterns, masks, and molds for various lithographic skills to achieve sub-10 nm resolutions. This approach is a synergetic combination of the "top-down" and "bottom-up" approaches, and superior to the previous techniques in terms of smaller feature size and better control. The objects for nanocrystal lithography are nanosized materials made by bottom-up approaches such as solution-based and gas phase syntheses. The Langmuir-Blodgett technique can be applied to the nanoscale objects for making uniform and directional alignments with controlled density and pitch, and the resulting arrays are deposited on the various substrates. By the kind of "top-down" lithographic techniques, we can specify nanocrystal lithography as the following: (a) direct patterning, (b) nanocrystal mask, and (c) nanocrystal imprint.

EXAMPLE 11

Direct Patterning of Nanocrystal Arrays

Langmuir-Blodgett monolayers can be directly deposited onto the patterned substrates, or on the flat substances followed by lithographic treatments. For example, Pt dot arrays on silica substrates can be regarded as 2-dimensional model catalysts to address various reactions on the surface. Electron beam lithography was used for generating the Pt nanoparticles with 30 nm diameters and 100 nm periodicity as the maximum resolution. We have fabricated the same arrays of monodisperse Pt nanocubes with 7 nm diameters on a silicon substrate by LB method, and the resulting density of Pt surfaces was estimated as 50 times larger than that obtained by corresponding "top-down" process.

The LB technique is able to control the directionality and density of nanocrystals. But if the positional control of each object is possible, the nanoscale materials can be directly incorporated into the silicon-based device structures, and enable the fabrication of integrated nanosystems with current technology. For this purpose, we consider additional driving forces such as chemical, magnetic, and electronic fluxes as well as applying secondary perpendicular surface pressure to be relevant.

Patterning Through Nanocrystal Masks

Closed packed nanoparticles and nanowires can serve as shadow masks to create nanoscale arrays. The deposited patterns are mainly defined by the size and spacing of the nanocrystals used in the masks. We suggest that addition of organic surfactants can tune the pitch of the nanowire masks more accurately. The organic residues are removed by $O_2$ plasma treatment. Nanosphere lithography is also classified in this category with the feature size of 20-1000 nm range. Additionally, patterning through these nanocrystal masks is expected to generate unique nanoscale structures of metal and other materials on the substrates, as well as to make different alignment of nanostructures.

EXAMPLE 12

Nanocrystal Imprint

Nanoimprint lithography attracts much attention due to their high throughput with easy operation at a low cost. We propose the nanocrystal arrays as original patterns. The 2-dimensional superlattice structure of nanocrystals is transferred to the polymer such as PDMS (poly(dimethylsiloxane)) or thin Si substrates. Dense $SiO_2$ layers are deposited on top of it by either sputtering or low pressure chemical vapor deposition. The $SiO_2$ replica of the nanocrystals is fabricated by etching the substrates. The patterns are repetitively imprinted by the resulting $SiO_2$ stamps, followed by deposition of metal and metal oxide. The interesting point of this nanocrystal imprint technique is that only the patterns of the nanocrystals are duplicated regardless of material composition. For example, monodisperse Pt nanorods synthesis has not been explored so far by solution-based technique, but the same Pt rod structures can be easily patterned by nanocrystal imprint using gold nanorod structures and subsequent Pt deposition.

Combination of the nanostructures with LB technique (a representative of bottom-up approach) and optical and non-optical lithography (that of top-down approach) offers virtually any nanoscale materials into the highly integrated and hierarchically organized electronic devices based on current microelectronics technology. If the nanoscale materials are easily handled in this way, the impact would be enormous in various fields, and diminish the period drastically for the high performance "nanoelectronic" devices into the real market.

SERS Substrate for Arsenic Sensing in Water

In the next example, hot spot frequency on a given SERS substrate is maximized with the assembly of shape-controlled metal nanocrystals using Langmuir-Blodgett (LB) compression (assembly). As explained above, LB assembly involves the isothermal compression of colloidal nanostructures suspended at an air-water interface. Dense, organized arrays of metal nanostructures behave as high surface area SERS substrates that can achieve large Raman enhancement factors. LB assembly is used in the present invention to create close-packed monolayers of polyhedral silver nanocrystals with various shapes (cubes, cuboctahedra, and octahedra) to design reproducible, regular, and highly active SERS substrates.

In addition, the performance of the sensing scheme of the present invention is a function of the ability to bind arsenate ions in close proximity to the silver surface, where the incident electromagnetic radiation is localized. The Raman enhancement factor decreases exponentially with the distance between the analyte molecule and the metal surface. Previous attempts at utilizing SERS to detect arsenic report the binding of arsenate ions directly onto the silver surface, but achieved low sensitivities and poor signal-to-noise ratios.

PVP ($M_w$~55,000) is used as an attractive ligand for binding arsenate ions in aqueous solution. PVP is grafted onto the silver surface as result of our polyhedral nanocrystal synthesis, where it behaves as a particle stabilizer and shape control agent. Results indicate that the pyrrolidone units of PVP, with slight heating of the analyte droplet, readily bind to arsenate and arsenite ions in solution and are effective in increasing the observed SERS effect.

The above-described SERS substrates of the present invention are relatively stable and can be prepared a few days before carrying out Raman detection.

Colloidal solutions of different polyhedral shapes were prepared according to the method detailed in FIG. 26A.

Monodisperse colloidal solutions of silver nanocrystals were synthesized with regular polyhedral shapes and bound entirely by {100} and {111} facets of the fcc crystal lattice. By extending the polyol reaction for a given time period, various polyhedral shapes capped with {100} and {111} faces can be obtained in high yield. FIG. 26A shows a schematic of the nucleation and growth process, in which silver continuously deposits onto the {100} facet to eventually result in a completely {111}-bound octahedron.

These nanocrystals are synthesized using the polyol method, where the metal salt is reduced by a diol solvent at near-reflux temperatures ($\approx 180°$ C.) in the presence of a polymeric stabilizing agent. Poly (vinyl pyrrolidone) (PVP) is used as the capping polymer. In a typical synthesis, silver nitrate and PVP are dissolved separately and then injected periodically into a solution of hot pentanediol. Depending on how long these sequential additions are continued, specific polyhedral shapes can be obtained in high yield.

As seen in the scanning electron microscopy (SEM) images in FIGS. 26B-26F, a variety of nanocrystal shapes with uniform sizes may be synthesized: cubes 50 (d$\approx$80 nm), truncated cubes 52 (d$\approx$120 nm), cuboctahedra 54 (d$\approx$150-200 nm), truncated octahedra 56 (d$\approx$200-250 nm), and octahedra 58 (d$\approx$250-300 nm). Transmission electron microscopy images confirm that the polyhedra are single-crystalline and exhibit atomically defined facets with sharp edges and corners. Metallic octahedral nanocrystals are the majority product. On the basis of energetic considerations, the optimal particle shape for an fcc metal is a truncated octahedron with regular hexagonal faces. Thus, the formation of octahedra suggests that the polyhedral nanocrystals observed here result from a kinetically limited reaction equilibrium.

This growth mechanism, was further shown with UV/Vis absorption spectrometry (Agilent, UV/Visible Chemstation) to evaluate shape-specific LSPs in the optical frequencies.

FIG. 27 displays a plot of the dipolar plasmon wavelength as a function of reaction time. This LSP mode is associated with nanoparticle volume and undergoes a red shift with increasing diameter. The graph indicates that shape evolution occurs in two steps: fast nucleation, which occurs at an exponential rate, and slow growth, which occurs at a linear rate. Initially, small silver particles (<10 nm) nucleate and develop into nanocubes bound by {100} planes, which are thought to be selectively stabilized by adsorbed PVP. As the reaction is continued, silver deposits selectively onto the {100} nanocrystal facets rather than growing in a layer-by-layer fashion (see FIG. 26A) The {111}-capped corners of the nanocube are stabilized during this growth period in which the nanocrystal evolves from a {100}-bound cube to a {111}-bound octahedron. The stability of both {100} and {111} planes in the presence of PVP indicates that shape control may not be explicitly dictated by the capping polymer. Rather, preferential crystal growth seems to result from a kinetically limited equilibrium influenced heavily by reaction parameters such as temperature, reactant concentration, and reactant molar ratios.

The LB assembly was carried out according to the method detailed in FIGS. 28A-C, showing the bottom-up fabrication of large-area, two dimensional plasmonic materials composed of polyhedral Ag NCs, where plasmon resonances can be explicitly tuned by means of NC shape and arrangement. In the LB technique, a colloidal solution of NCs is spread at an air-water interface, forming an isotropic monolayer of floating NCs whose density is controlled by surface pressure ($\pi$) through isothermal compression or expansion. Close-packed arrays of NCs are obtained by compressing the fluid-supported film to maximum surface pressures of $\pi \sim 14$ mN m$^{-1}$.

FIG. 28A-C shows scanning electron microscope (SEM) images of superlattices composed of truncated cubes (d~120 nm), cuboctahedra (d~150 nm) and octahedral (d~250 nm) Ag NCs. Close-packed NC monolayers in these SEM images were obtained after isothermal compression of an LB NC monolayer at a compression rate of ~10 cm$^2$ min$^{-1}$ to a final surface pressure of $\pi \sim 14$ mN m$^{-1}$. The insets show individual nanocrystal geometry (top), fast Fourier transform images indicating long-range order within each (middle) and close-up SEM images showing the nanocrystal unit cell (bottom). The different polyhedral shapes are synthesized by a modified polyol process shown in FIG. 27. Lattice packing and dimensions are dictated by the choice of NC building blocks. Truncated cubes tend to assemble face to face to form a square lattice, similar to packing architectures observed for iron particles and zeolite arrays (FIG. 28A). For cuboctahedra—a more truncated polyhedral building block—this square lattice shears to form a rhombohedral unit cell (FIG. 28B). Octahedra adopt a hexagonal lattice on compression, lying flat on their triangular facets such that three NCs form an interlocked triangle (FIG. 28C). Correspondingly, when considering the complementary geometries of the interstitial spaces within the lattice, each NC building block also gives rise to unique interstitial structures. Optical transmission and reflectance measurements indicate that these three different symmetries of NC packing profoundly affect the manner in which light interacts with the NC films. The distinct surface plasmon modes of the differently shaped building blocks and the geometries in which they are assembled contribute to collective plasmonic properties that are unique to each LB film.

To understand the nature of plasmon coupling within these superlattices and explore tunability of the resulting optical response, the optical properties of cuboctahedra NC monolayers were capitalized. In colloidal solution, cuboctahedra NCs exhibit a unique electromagnetic response owing to their non-spherical geometries, displaying sharp plasmon resonances in the visible regime corresponding to charge polarizations localized at the atomically defined corners, edges and facets of the particles. Within a two-dimensional lattice, however, plasmon coupling between NCs is expected to dominate the optical response, with increased electromagnetic coupling between NCs as interparticle distance is decreased. This relationship allows for a simple strategy to tailor the optical response of our superlattice structures during the assembly process, specifically by controlling surface pressure at the air-water interface to give different NC spacings.

The pressure-area isotherm for a typical compression experiment is shown in FIG. 29A, where changes in slope correspond to phase transitions of the NC film from gas to condensed-liquid to solid states. Snapshots of the cuboctahedra monolayer as it is compressed are shown in FIG. 29B-D, demonstrating the visually arresting color evolution of the film stemming from changes in the Plasmon response due to electromagnetic coupling between NCs. The intensity of the monolayer color at these varying surface pressures is quite surprising given that the film is only the thickness of a single NC; colloidal solutions of the cuboctahedra NCs at much higher concentrations exhibit light reflectance with intensities orders of magnitude lower. Isothermal compression was performed at a barrier speed of 10 cm² min⁻¹ for surface pressures of π<5 mN m⁻¹. For π>5 mN m⁻¹, compression was performed at a barrier speed of 5 cm² min⁻¹.

The collective plasmon properties of the NC film are entirely dependent on NC arrangement. To characterize this, samples of the NC monolayer characterized by dip-transfer onto solid supports at low (π~0 mN m⁻¹), intermediate (π~1 mN m⁻¹) and high surface pressures (π~14 mN m⁻¹) corresponding to different phases of the LB film. Snapshots of these fluid supported NC films, along with corresponding SEM images after transfer to a Si substrate during isothermal compression, are shown in FIG. 29B-D.

As NC density increases through mechanical compression of the film, the evolving coupled plasmon response of the superlattice results in vibrant color changes of the bulk NC film. For π~0 mN m⁻¹, the SEM image in FIG. 29B shows that the NCs self-organize into a hexagonal lattice with an interparticle spacing of ~40 nm and a lattice spacing of a ~230 nm. At low NC density, the cuboctahedra NCs experience hard-sphere interactions and spontaneously assemble into the hexagonal lattice. The distance between NCs is approximately the radius of gyration for two PVP layers, which is expected for as-synthesized Ag NCs that possess surfaces capped by adsorbed polymer. The steric nature of PVP allows for hard-sphere-like interactions between adjacent NCs, and the NCs pack into a highly uniform two-dimensional lattice.

As NC density increases, the cuboctahedra nucleate into small islands composed of between 1 and 10 NCs. The SEM image of the NC film obtained at π=1.0 mN m⁻¹ (FIG. 29C) shows that the monolayer comprises oligomers of between 1 and 10 NCs and on average approximately 4 NCs wide. At this threshold surface pressure, the compression force is high enough to overcome the steric barrier of the adsorbed PVP on the NC surfaces that prevented particle aggregation at lower surface pressures.

FIG. 29D shows an SEM image of the NC monolayer collected at π~14 mN m⁻¹. Here, NC density reaches a maximum with a distance between neighboring NCs of <5 nm and estimated to be ~2 nm when considering the chain length of adsorbed PVP on the Ag surface. At the maximum NC density, the Ag NCs adopt a crystalline close-packed superlattice. The monolayer appears highly reflective and is irreversibly compressed A unique feature of these NC monolayers is the ability to tune the plasmon response of the fluid-supported film across the visible range by controlling electromagnetic interaction. The nature of LB assembly offers the unprecedented opportunity to examine the evolution of NC film reflectance as interparticle spacing is continuously tuned. This may already be clearly observed from the digital images shown in FIG. 29B-D.

FIG. 30A-B shows the specular reflectance of the cuboctahedra superlattice at the air-water interface as it undergoes isothermal compression, with spectra grouped into low (π<0.5 mN m⁻¹) and high (0.5<π<14 mN m⁻¹) surface pressure regimes for clarity. In FIG. In FIG. 30B the spectra are offset for clarity. Total film area decreases from bottom to top for each graph. The backgrounds 70, 72 and 74 are used to highlight plasmon responses arising from quadrupolar coupling (72), higher-order mode coupling (70) and plasmon delocalization (74). FIG. 30C shows dark-field scattering spectra for the NC monolayers at the indicated surface pressures. Spectra are normalized and offset for clarity. FIGS. 30E-F show digital images of each film under dark-field illumination.

The reflectance lineshape of the fluid-supported monolayer differs greatly from that of the isotropic colloidal NC suspension (FIG. 30A, inset). It exhibits a broad dipolar resonance at $\lambda_{dip}$~790 nm and a quadrupolar resonance at $\lambda_{quad}$~480 nm. At low pressures, a single plasmon resonance peak associated with quadrupolar mode coupling dominates the optical response of the water-supported NC film (shaded region 72 in FIG. 30A-30B). As the film is compressed, this peak blue-shifts and increases in reflectance intensity, indicating stronger near-field interactions between NCs, as expected. This peak reaches a maximum intensity just as the film transitions from gas to liquid (corresponding to point b in FIG. 29A), with FWHM=48 nm at ~490 nm. As surface pressure increases with further compression of the monolayer, higher-order mode coupling gives rise to reflectance peaks at shorter wavelengths (shaded region 70 in FIG. 30A-30B). In addition, a new broad reflectance peak corresponding to plasmon delocalization over multiple NCs arises in the longer wavelengths (shaded region 74 in FIG. 30B). When NC density approaches the close-packed limit at π~14 mN m⁻¹ (point d in FIG. 29A), the reflectance spectrum approaches a continuum with uniform intensity rather than exhibiting distinct resonance modes. Clearly, these changes in wavelength and intensity of the film's plasmonic response indicate complex near-field interactions, which are dictated by more than a simple distance dependence.

FIGS. 31A-C show SEM images of silver shapes after Langmuir Blodgett assembly according to the present invention: cubes (FIG. 31A), cuboctahedra (FIG. 31B), and octahedra (FIG. 31C). After compression to a surface pressure of Π=14 mN/m, the nanocrystal monolayers were transferred onto 6 mm×6 mm silicon supports. To carry out detection experiments, the nanocrystal substrates were exposed to analyte molecules by incubation and subsequent Raman detection in solution. Raman detection was performed using a Renishaw micro-Raman system using a 532 nm diode-pumped solid state laser as the excitation source, with an estimated power of ~20 mW. Raman signal was collected in reflectance mode using a 50× objective.

Results demonstrate that close-packed monolayers of silver octahedra give the highest enhancement factors. To characterize the effect of nanocrystal shape on SERS intensities, nanocrystal arrays of cubes, cuboctahedra, and octahedral were exposed. Using a thermal-evaporated silver film as a reference, enhancement factors were estimated according to:

$$EF_{shape}=(I_{shape})/(I_{film}) \times [film]/[shape]$$

where $I_{shape}$ and $I_{film}$ are the intensity of the SERS signal at 800 cm⁻¹ for the nanocrystal monolayers and silver film, respectively, and [film] and [shape] are the concentration of the analyte solutions. The approximated enhancement factors are as follows: $EF_{octahedra}$~60×10³; $EF_{cuboctahedra}$~17×10³; $EF_{cube}$~3.7×10³.

Using the LB-prepared assembly of silver octahedra, $u_1$ (As—O) symmetric stretch at 800 cm⁻¹ for arsenate levels as low as 1.8 ppb was observed. FIGS. 32A-B show the results of surface enhanced Raman spectroscopy on silver octahedra films. FIG. 32A shows various concentrations of $HAsO_4^{2-}$ in solution, and FIG. 32B shows comparison of As (III) and As (V) at solutions at 20 mM. The peak visible at 680 cm⁻¹ is assigned to the C-C ring stretch associated with the adsorbed PVP. SERS detection performed for various concentrations of the arsenate species indicate the viability of utilizing our chemical detection scheme for quantitative field measurements of arsenate concentration. Identical concentration studies were conducted on cube and cuboctahedra nanocrystal monolayers yielding similar results lower sensitivities, as expected.

Using the octahedra nanocrystal SERS substrates of the present invention, the unique ability to distinguish between the As(V) and As(III) ionic species was demonstrated. The nanocrystal film was exposed to an aqueous solution of both arsenate and arsenite ion in equal concentration. Stretching modes for the two molecules with different symmetries, and thus unique Raman bands, can be seen at 800 cm$^{-1}$ and 750 cm$^{-1}$ for the As(III) and As(V) ions respectively in FIG. 32B. Resolution of these two different peaks should allow for additional quantification of each of the species present in groundwater samples.

The schematic in FIG. 33 describes the structure of an embodiment of the SERS substrate sensor 100 in accordance with the present invention, which provides high sensitivity to both arsenate and arsenite. The sensor 100 includes a silicon wafer substrate 104 with a monolayer 102 of one or more close-packed arrays of well faceted monodisperse silver nanoparticles 106. Each of the silver nanocrystals 106 are protected with a layer 108 of protective polymer (PVP surface coating), which both protects the silver from oxidation and allows the transfer of arsenic to the silver surface to facilitate arsenate sensing.

The substrate 104 comprises a silicon wafer 5 mm×5 mm×0.5 mm. However, it is appreciated that the exact size and nature of the substrate is not critical to the function of the device, and that any number of substrates known in the art may be used to support the monolayer 102 which form the active component of the sensor 100.

EXAMPLE 1

Nanoparticle Synthesis

Nanocrystal synthesis: Silver nitrate (0.40 g) and copper (II) chloride (0.86 mg) were dissolved in 1,5-pentanediol (10 mL) in a glass vial. In a separate vial, PVP (Mw=55000 amu, 0.20 g) was dissolved in 1,5-pentanediol (10 mL). Using a temperature-controlled silicone oil bath, 1,5-pentanediol (20 mL) was heated for 10 min at 193° C. The two precursor solutions were then injected into the hot reaction flask at different rates: 500 mL of the silver nitrate solution every minute and 250 mL of the PVP solution every 30 seconds. For nanocubes, this addition was stopped once the solution turned opaque (~6 minutes). For cuboctahedra, and octahedra the addition of precursor solutions was continued for a longer period of time (30-45 minutes for cube-octahedra and 60-75 min for octahedral nanocrystals).

EXAMPLE 2

Nanoparticle Purification

Average reactions yield product shape distributions where the dominant shape represents 80-95% of the sample, while many of the impurity shapes are larger polycrystals or wires. These larger impurities may be removed by vacuum filtration using progressively smaller Durapore™ filters (5.0 µm, 0.65 µm, 0.45 µm, 0.22 µm) supported by a glass frit. To filter the particles, they are first transferred into a 0.02 wt % solution of PVP in water, where the final volume of this filtrate solution is 10× the volume of the original reaction solution. After the filtration is complete, the purified nanoparticle solutions are stored as suspensions in ethanol.

EXAMPLE 3

Nanoparticle Assembly

Nanoparticle assembly was carried out using a Nima Technology Langmuir Blodgett Trough. The nanocrystals were first transferred from ethanol to chloroform by centrifuging the ethanolic solution for 20 minutes at 3,000 rpm, and removing all but a few drops of the supernatant. The particles were then sonicated to bring them back into suspension and chloroform was added dropwise to a volume of ~5 mL. The suspension of particles in chloroform was dispersed on the surface of the water dropwise, and the chloroform was allowed to evaporate for at least ½ hour. The film was then compressed at 15 cm$^2$/min until the surface pressure was 13.5 mN/cm$^2$ (for dilute samples lower surface pressure was used). This close-packed film was transferred to silicon substrates via a mechanical dipper moving at 2 mm/min.

The results demonstrate Langmuir-Blodgett assemblies of polyhedral silver nanocrystals as highly sensitive SERS substrates for chemical detection of various arsenic species in water. These substrates are portable, disposable, easily prepared, and can be readily used for field detection of arsenic at detection levels of parts per billion.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art. In the description and in the claims, reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A sensor, comprising:
a substrate;
the substrate comprising at least one high-density monolayer of polyhedral silver nanocrystals;
wherein each of the nanocrystals comprise a layer of polyvinypyrrolidone (PVP) on its surface;
wherein the nanocrystals are aligned in the monolayer to have uniform interparticle spacing and directional alignment with controlled density and pitch; and
wherein the PVP layer is configured to allow for transfer of one or more chemical compounds to the high-density monolayer of polyhedral silver nanocrystals for sensing the one or more chemical compounds.

2. A sensor as recited in claim 1, wherein the nanocrystals comprise octahedra.

3. A sensor as recited in claim 1, wherein the nanocrystals have a shape selected from the group consisting of truncated cubes, cuboctahedra, truncated octahedral, and octahedra.

4. A sensor as recited in claim 1, wherein the substrate comprises a plurality of monolayers of polyhedral silver nanocrystals compressed as close-packed parallel arrays, wherein longitudinal axes of the nanocrystals are aligned perpendicular to a compression direction of the monolayer.

5. A sensor as recited in claim 1, wherein said nanocrystals are shape-controlled using Langmuir-Blodgett compression.

6. A sensor as recited in claim 1, wherein said PVP is grafted onto the silver surface by polyhedral nanocrystal synthesis.

7. A sensor as recited in claim 1, wherein the substrate comprises a surface-enhanced Raman spectroscopy (SERS) substrate.

8. A sensor as recited in claim 6:
wherein prior to synthesis, the nanocrystals of the nanocrystal monolayer comprise an exposed silver surface;
wherein the PVP layer comprises an analyte solution of polyvinypyrrolidone (PVP) that is deposited on the exposed silver surface of the nanocrystal monolayer;
wherein the one or more chemical compounds comprises arsenate and arsenite; and
wherein said analyte solution is configured to allow transfer of arsenic to facilitate binding of both arsenate and arsenite near the exposed silver surface.

9. A sensor as recited in claim 6, wherein incident electromagnetic radiation is localized on said silver surface.

10. A sensor as recited in claim 1, wherein the high density monolayer of nanocrystals comprises a uniform interparticle spacing of less than approximately 40 nm.

11. A sensor as recited in claim 10, wherein the high density monolayer of nanocrystals comprises a uniform interparticle spacing of less than approximately 5 nm.

\* \* \* \* \*